United States Patent [19]

Misawa et al.

[11] Patent Number: 5,589,581
[45] Date of Patent: Dec. 31, 1996

[54] DNA SEQUENCES USEFUL FOR THE SYNTHESIS OF CAROTENOIDS

[75] Inventors: Norihiko Misawa; Kazuo Kobayashi; Katsumi Nakamura, all of Takasaki, Japan

[73] Assignee: Kirin Beer Kabushiki Kaisha, Tokyo-To, Japan

[21] Appl. No.: 209,617

[22] Filed: Mar. 10, 1994

Related U.S. Application Data

[63] Continuation of Ser. No. 519,011, Apr. 19, 1990, abandoned.

[30] Foreign Application Priority Data

Apr. 21, 1989 [JP] Japan ..................... 1-103078
Mar. 5, 1990 [JP] Japan ..................... 2-53255

[51] Int. Cl.$^6$ .......................... C07H 21/04; C12N 11/18; C12N 9/02; C12N 9/90
[52] U.S. Cl. ................ 536/23.2; 536/23.1; 536/23.7; 536/23.74; 536/23.6; 435/175; 435/172.3; 435/320.1; 435/252.3; 435/189; 435/233
[58] Field of Search .................... 536/23.2, 23.1, 536/23.7, 23.74, 23.6; 930/240; 935/9, 14; 435/175, 233, 320.1, 252.3, 189

[56] References Cited

FOREIGN PATENT DOCUMENTS 1113079  9/1991  WIPO .

OTHER PUBLICATIONS

*Hackh's Chemical Dictionary*, Fourth edition., Grant (ed.), 1969 McGraw-Hill Book Co. New York, p. 361.
Berger et al. (eds.) 1987. in: *Methods in Enzymology*, Academic Press. San Diego, pp. 33–110, 668, and 669.
Misawa et al. 1990. J. Bacteriol. 172, 6704–6712.
Giuliano et al. 1986. Molec. Gen. Genet. 213, 78–83.
Maniatis et al. (eds.) in: *Molecular Cloning. A Laboratory Manual*. Cold Spring Harbor Laboratory. Cold Spring Harbor Laboratory. NY. pp. 86–87. (1982).
Ogura, K. *J. Biochem* 72:1101–1108 (1972).
Grubb, P. W., *Patents in Chemistry and Biotechnology*, (Clarendon Press–Oxford 1986) pp. 158–163.
Camara, Bilal et al., Eur. J. Biochem 127:255–258 (1982).
Aragon, C. M. G. et al., *Eur. J. Biochem.* 63:71–75 (1976).
G. Thiry, J. Gen. Microbiology, 130, 1623–1631 (1984).
K. Perry, et al., J. of Bacteriology, 168(2): 607–612 (Nov. 1986).
R. W. Tuveson, et al., J. of Bacteriology, 170 (10):4675–4680 (Oct. 1988).
G. A. Armstrong, et al., Mol. Gen. Genet. 216: 254–268 (1989).
G. E. Bartley et al., J. of Biological Chemistry, 264(22): 13109–13113 (1989).

*Primary Examiner*—Christopher S. F. Low
*Attorney, Agent, or Firm*—Ladas & Parry

[57] ABSTRACT

Disclosed are DNA sequences which are useful for the synthesis of carotenoids such as lycopene, β-carotene, zeaxanthin or zeaxanthin-diglucoside, that is, DNA sequences encoding carotenoid biosynthesis enzymes. These DNA sequences are the sequences ①–⑥, respectively, shown in the specification.

Also disclosed is a process for producing a carotenoid compound which is selected from the group consisting of prephytoene pyrophosphate, phytoene, lycopene, β-carotene, zeaxanthin and zeaxanthin-diglucoside, which comprises transforming a host with at least one of the DNA sequences ①–⑥ described above and culturing the transformant.

6 Claims, 19 Drawing Sheets

```
     230       240       250       260       270       280
ATGACGGTCTGCGCAAAAAACACGTTCATCTCACTCGCGATGCTGCGGAGCAGTTACTG
MetThrValCysAlaLysLysHisValHisLeuThrArgAspAlaAlaGluGlnLeuLeu
↑
A
     290       300       310       320       330       340
GCTGATATTGATCGACGCCTTGATCAGTTATTGCCCGTGGAGGGAGAACGGGATGTTGTG
AlaAspIleAspArgArgLeuAspGlnLeuLeuProValGluGlyGluArgAspValVal 350       360       370       380       390       400
GGTGCCGCGATGCGTGAAGGTGCGCTGGCACCGGGAAAACGTATTCGCCCCATGTTGCTG
GlyAlaAlaMetArgGluGlyAlaLeuAlaProGlyLysArgIleArgProMetLeuLeu 410       420       430       440       450       460
TTGCTGACCGCCCGCGATCTGGGTTGCGCTGTCAGCCATGACGGATTACTGGATTTGGCC
LeuLeuThrAlaArgAspLeuGlyCysAlaValSerHisAspGlyLeuLeuAspLeuAla 470       480       490       500       510       520
TGTGCGGTGGAAATGGTCCACGCGGCTTCGCTGATCCTTGACGATATGCCCTGCATGGAC
CysAlaValGluMetValHisAlaAlaSerLeuIleLeuAspAspMetProCysMetAsp 530       540       550       560       570       580
GATGCGAAGCTGCGGCGCGGACGCCCTACCATTCATTCTCATTACGGAGAGCATGTGGCA
AspAlaLysLeuArgArgGlyArgProThrIleHisSerHisTyrGlyGluHisValAla 590       600       610       620       630       640
ATACTGGCGGCGGTTGCCTTGCTGAGTAAAGCCTTTGGCGTAATTGCCGATGCAGATGGC
IleLeuAlaAlaValAlaLeuLeuSerLysAlaPheGlyValIleAlaAspAlaAspGly 650       660       670       680       690       700
CTCACGCCGCTGGCAAAAAATCGGGCGGTTTCTGAACTGTCAAACGCCATCGGCATGCAA
LeuThrProLeuAlaLysAsnArgAlaValSerGluLeuSerAsnAlaIleGlyMetGln 710       720       730       740       750       760
GGATTGGTTCAGGGTCAGTTCAAGGATCTGTCTGAAGGGGATAAGCCGCGCAGCGCTGAA
GlyLeuValGlnGlyGlnPheLysAspLeuSerGluGlyAspLysProArgSerAlaGlu 770       780       790       800       810       820
GCTATTTTGATGACGAATCACTTTAAAACCAGCACGCTGTTTTGTGCCTCCATGCAGATG
AlaIleLeuMetThrAsnHisPheLysThrSerThrLeuPheCysAlaSerMetGlnMet 830       840       850       860       870       880
GCCTCGATTGTTGCGAATGCCTCCAGCGAAGCGCGTGATTGCCTGCATCGTTTTTCACTT
AlaSerIleValAlaAsnAlaSerSerGluAlaArgAspCysLeuHisArgPheSerLeu
```

FIG. 1 (a)

```
      890       900       910       920       930       940
GATCTTGGTCAGGCATTTCAACTGCTGGACGATTTGACCGATGGCATGACCGACACCGGT
AspLeuGlyGlnAlaPheGlnLeuLeuAspAspLeuThrAspGlyMetThrAspThrGly 950       960       970       980       990      1000
AAGGATAGCAATCAGGACGCCGGTAAATCGACGCTGGTCAATCTGTTAGGCCCGAGGGCG
LysAspSerAsnGlnAspAlaGlyLysSerThrLeuValAsnLeuLeuGlyProArgAla 1010      1020      1030      1040      1050      1060
GTTGAAGAACGTCTGAGACAACATCTTCAGCTTGCCAGTGAGCATCTCTCTGCGGCCTGC
ValGluGluArgLeuArgGlnHisLeuGlnLeuAlaSerGluHisLeuSerAlaAlaCys 1070      1080      1090      1100      1110      1120
CAACACGGGCACGCCACTCAACATTTTATTCAGGCCTGGTTTGACAAAAAACTCGCTGCC
GlnHisGlyHisAlaThrGlnHisPheIleGlnAlaTrpPheAspLysLysLeuAlaAla

1130
GTCAGTTAA
ValSer***
    ↑
    B
```

FIG. 1 (b)

```
      1150       1160       1170       1180       1190       1200
ATGAGCCATTTCGCGGCGATCGCACCGCCTTTTTACAGCCATGTTCGCGCATTACAGAAT
MetSerHisPheAlaAlaIleAlaProProPheTyrSerHisValArgAlaLeuGlnAsn
↑
C
      1210       1220       1230       1240       1250       1260
CTCGCTCAGGAACTGGTCGCGCGCGGTCATCGGGTGACCTTTATTCAGCAATACGATATT
LeuAlaGlnGluLeuValAlaArgGlyHisArgValThrPheIleGlnGlnTyrAspIle 1270       1280       1290       1300       1310       1320
AAACACTTGATCGATAGCGAAACCATTGGATTTCATTCCGTCGGGACAGACAGCCATCCC
LysHisLeuIleAspSerGluThrIleGlyPheHisSerValGlyThrAspSerHisPro 1330       1340       1350       1360       1370       1380
CCCGGCGCGTTAACGCGCGTGCTACACCTGGCGGCTCATCCTCTGGGGCCGTCAATGCTG
ProGlyAlaLeuThrArgValLeuHisLeuAlaAlaHisProLeuGlyProSerMetLeu 1390       1400       1410       1420       1430       1440
AAGCTCATCAATGAAATGGCGCGCACCACCGATATGCTGTGCCGCGAACTCCCCCAGGCA
LysLeuIleAsnGluMetAlaArgThrThrAspMetLeuCysArgGluLeuProGlnAla 1450       1460       1470       1480       1490       1500
TTTAACGATCTGGCCGTCGATGGCGTCATTGTTGATCAAATGGAACCGGCAGGCGCGCTC
PheAsnAspLeuAlaValAspGlyValIleValAspGlnMetGluProAlaGlyAlaLeu 1510       1520       1530       1540       1550       1560
GTTGCTGAAGCACTGGGACTGCCGTTTATCTCTGTCGCCTGCGCGCTGCCTCTCAATCGT
ValAlaGluAlaLeuGlyLeuProPheIleSerValAlaCysAlaLeuProLeuAsnArg 1570       1580       1590       1600       1610       1620
GAACCGGATATGCCCCTGGCGGTTATGCCTTTCGAATACGGGACCAGCGACGCGGCTCGC
GluProAspMetProLeuAlaValMetProPheGluTyrGlyThrSerAspAlaAlaArg 1630       1640       1650       1660       1670       1680
GAACGTTATGCCGCCAGTGAAAAAATTTATGACTGGCTAATGCGTCGTCATGACCGTGTC
GluArgTyrAlaAlaSerGluLysIleTyrAspTrpLeuMetArgArgHisAspArgVal 1690       1700       1710       1720       1730       1740
ATTGCCGAACACAGCCACAGAATGGGCTTAGCCCCCCGGCAAAAGCTTCACCAGTGTTTT
IleAlaGluHisSerHisArgMetGlyLeuAlaProArgGlnLysLeuHisGlnCysPhe 1750       1760       1770       1780       1790       1800
TCGCCACTGGCGCAAATCAGCCAGCTTGTTCCTGAACTGGATTTTCCCCGCAAAGCGTTA
SerProLeuAlaGlnIleSerGlnLeuValProGluLeuAspPheProArgLysAlaLeu
```

FIG. 2 (a)

```
      2430        2440        2450        2460        2470        2480
ATGCAACCGCATTATGATCTGATTCTCGTGGGGGCTGGACTCGCGAATGGCCTTATCGCC
MetGlnProHisTyrAspLeuIleLeuValGlyAlaGlyLeuAlaAsnGlyLeuIleAla
↑
E
      2490        2500        2510        2520        2530        2540
CTGCGTCTTCAGCAGCAGCAACCTGATATGCGTATTTTGCTTATCGACGCCGCACCCCAG
LeuArgLeuGlnGlnGlnGlnProAspMetArgIleLeuLeuIleAspAlaAlaProGln 2550        2560        2570        2580        2590        2600
GCGGGCGGGAATCATACGTGGTCATTTCACCACGATGATTTGACTGAGAGCCAACATCGT
AlaGlyGlyAsnHisThrTrpSerPheHisHisAspAspLeuThrGluSerGlnHisArg 2610        2620        2630        2640        2650        2660
TGGATAGCTCCGCTGGTGGTTCATCACTGGCCCGACTATCAGGTACGCTTTCCCACACGC
TrpIleAlaProLeuValValHisHisTrpProAspTyrGlnValArgPheProThrArg 2670        2680        2690        2700        2710        2720
CGTCGTAAGCTGAACAGCGGCTACTTTTGTATTACTTCTCAGCGTTTCGCTGAGGTTTTA
ArgArgLysLeuAsnSerGlyTyrPheCysIleThrSerGlnArgPheAlaGluValLeu 2730        2740        2750        2760        2770        2780
CAGCGACAGTTTGGCCCGCACTTGTGGATGGATACCGCGGTCGCAGAGGTTAATGCGGAA
GlnArgGlnPheGlyProHisLeuTrpMetAspThrAlaValAlaGluValAsnAlaGlu 2790        2800        2810        2820        2830        2840
TCTGTTCGGTTGAAAAAGGGTCAGGTTATCGGTGCCCGCGCGGTGATTGACGGGCGGGGT
SerValArgLeuLysLysGlyGlnValIleGlyAlaArgAlaValIleAspGlyArgGly 2850        2860        2870        2880        2890        2900
TATGCGGCAAATTCAGCACTGAGCGTGGGCTTCCAGGCGTTTATTGGCCAGGAATGGCGA
TyrAlaAlaAsnSerAlaLeuSerValGlyPheGlnAlaPheIleGlyGlnGluTrpArg 2910        2920        2930        2940        2950        2960
TTGAGCCACCCGCATGGTTTATCGTCTCCCATTATCATGGATGCCACGGTCGATCAGCAA
LeuSerHisProHisGlyLeuSerSerProIleIleMetAspAlaThrValAspGlnGln 2970        2980        2990        3000        3010        3020
AATGGTTATCGCTTCGTGTACAGCCTGCCGCTCTCGCCGACCAGATTGTTAATTGAAGAC
AsnGlyTyrArgPheValTyrSerLeuProLeuSerProThrArgLeuLeuIleGluAsp 3030        3040        3050        3060        3070        3080
ACGCACTATATTGATAATGCGACATTAGATCCTGAATGCGCGCGGCAAAATATTTGCGAC
ThrHisTyrIleAspAsnAlaThrLeuAspProGluCysAlaArgGlnAsnIleCysAsp
```

FIG. 3 (a)

```
         3090      3100      3110      3120      3130      3140
TATGCCGCGCAACAGGGTTGGCAGCTTCAGACACTGCTGCGAGAAGAACAGGGCGCCTTA
TyrAlaAlaGlnGlnGlyTrpGlnLeuGlnThrLeuLeuArgGluGluGlnGlyAlaLeu 3150      3160      3170      3180      3190      3200
CCCATTACTCTGTCGGGCAATGCCGACGCATTCTGGCAGCAGCGCCCCCTGGCCTGTAGT
ProIleThrLeuSerGlyAsnAlaAspAlaPheTrpGlnGlnArgProLeuAlaCysSer 3210      3220      3230      3240      3250      3260
GGATTACGTGCCGGTCTGTTCCATCCTACCACCGGCTATTCACTGCCGCTGGCGGTTGCC
GlyLeuArgAlaGlyLeuPheHisProThrThrGlyTyrSerLeuProLeuAlaValAla 3270      3280      3290      3300      3310      3320
GTGGCCGACCGCCTGAGTGCACTTGATGTCTTTACGTCGGCCTCAATTCACCATGCCATT
ValAlaAspArgLeuSerAlaLeuAspValPheThrSerAlaSerIleHisHisAlaIle 3330      3340      3350      3360      3370      3380
ACGCATTTTGCCCGCGAGCGCTGGCAGCAGCAGGGCTTTTTCCGCATGCTGAATCGCATG
ThrHisPheAlaArgGluArgTrpGlnGlnGlnGlyPhePheArgMetLeuAsnArgMet 3390      3400      3410      3420      3430      3440
CTGTTTTTAGCCGGACCCGCCGATTCACGCTGGCGGGTTATGCAGCGTTTTTATGGTTTA
LeuPheLeuAlaGlyProAlaAspSerArgTrpArgValMetGlnArgPheTyrGlyLeu 3450      3460      3470      3480      3490      3500
CCTGAAGATTTAATTGCCCGTTTTTATGCGGGAAAACTCACGCTGACCGATCGGCTACGT
ProGluAspLeuIleAlaArgPheTyrAlaGlyLysLeuThrLeuThrAspArgLeuArg 3510      3520      3530      3540      3550      3560
ATTCTGAGCGGCAAGCCGCCTGTTCCGGTATTAGCAGCATTGCAAGCCATTATGACGACT
IleLeuSerGlyLysProProValProValLeuAlaAlaLeuGlnAlaIleMetThrThr

3570
CATCGTTAA
HisArg***
    ↑
    F                FIG. 3 (b)
```

```
      3590       3600       3610       3620       3630       3640
 ATGAAACCAACTACGGTAATTGGTGCAGGCTTCGGTGGCCTGGCACTGGCAATTCGTCTA
 MetLysProThrThrValIleGlyAlaGlyPheGlyGlyLeuAlaLeuAlaIleArgLeu
↑
G
      3650       3660       3670       3680       3690       3700
 CAAGCTGCGGGGATCCCCGTCTTACTGCTTGAACAACGTGATAAACCCGGCGGTCGGGCT
 GlnAlaAlaGlyIleProValLeuLeuLeuGluGln.\rgAspLysProGlyGlyArgAla 3710       3720       3730       3740       3750       3760
 TATGTCTACGAGGATCAGGGGTTTACCTTTGATGCAGGCCCGACGGTTATCACCGATCCC
 TyrValTyrGluAspGlnGlyPheThrPheAspAlaGlyProThrValIleThrAspPro 3770       3780       3790       3800       3810       3820
 AGTGCCATTGAAGAACTGTTTGCACTGGCAGGAAAACAGTTAAAAGAGTATGTCGAACTG
 SerAlaIleGluGluLeuPheAlaLeuAlaGlyLysGlnLeuLysGluTyrValGluLeu 3830       3840       3850       3860       3870       3880
 CTGCCGGTTACGCCGTTTTACCGCCTGTGTTGGGAGTCAGGGAAGGTCTTTAATTACGAT
 LeuProValThrProPheTyrArgLeuCysTrpGluSerGlyLysValPheAsnTyrAsp 3890       3900       3910       3920       3930       3940
 AACGATCAAACCCGGCTCGAAGCGCAGATTCAGCAGTTTAATCCCCGCGATGTCGAAGGT
 AsnAspGlnThrArgLeuGluAlaGlnIleGlnGlnPheAsnProArgAspValGluGly 3950       3960       3970       3980       3990       4000
 TATCGTCAGTTTCTGGACTATTCACGCGCGGTGTTTAAAGAAGGCTATCTAAAGCTCGGT
 TyrArgGlnPheLeuAspTyrSerArgAlaValPheLysGluGlyTyrLeuLysLeuGly 4010       4020       4030       4040       4050       4060
 ACTGTCCCTTTTTTATCGTTCAGAGACATGCTTCGCGCCGCACCTCAACTGGCGAAACTG
 ThrValProPheLeuSerPheArgAspMetLeuArgAlaAlaProGlnLeuAlaLysLeu 4070       4080       4090       4100       4110       4120
 CAGGCATGGAGAAGCGTTTACAGTAAGGTTGCCAGTTACATCGAAGATGAACATCTGCGC
 GlnAlaTrpArgSerValTyrSerLysValAlaSerTyrIleGluAspGluHisLeuArg 4130       4140       4150       4160       4170       4180
 CAGGCGTTTTCTTTCCACTCGCTGTTGGTGGGCGGCAATCCCTTCGCCACCTCATCCATT
 GlnAlaPheSerPheHisSerLeuLeuValGlyGlyAsnProPheAlaThrSerSerIle 4190       4200       4210       4220       4230       4240
 TATACGTTGATACACGCGCTGGAGCGTGAGTGGGGCGTCTGGTTTCCGCGTGGCGGCACC
 TyrThrLeuIleHisAlaLeuGluArgGluTrpGlyValTrpPheProArgGlyGlyThr
```

F I G. 4 (a)

```
    4250      4260      4270      4280      4290      4300
GGCGCATTAGTTCAGGGGATGATAAAGCTGTTTCAGGATCTGGGTGGCGAAGTCGTGTTA
GlyAlaLeuValGlnGlyMetIleLysLeuPheGlnAspLeuGlyGlyGluValValLeu 4310      4320      4330      4340      4350      4360
AACGCCAGAGTCAGCCATATGGAAACGACAGGAAACAAGATTGAAGCCGTGCATTTAGAG
AsnAlaArgValSerHisMetGluThrThrGlyAsnLysIleGluAlaValHisLeuGlu 4370      4380      4390      4400      4410      4420
GACGGTCGCAGGTTCCTGACGCAAGCCGTCGCGTCAAATGCAGATGTGGTTCATACCTAT
AspGlyArgArgPheLeuThrGlnAlaValAlaSerAsnAlaAspValValHisThrTyr 4430      4440      4450      4460      4470      4480
CGCGACCTGTTAAGCCAGCACCCTGCCGCGGTTAAGCAGTCCAACAAACTGCAGACTAAG
ArgAspLeuLeuSerGlnHisProAlaAlaValLysGlnSerAsnLysLeuGlnThrLys 4490      4500      4510      4520      4530      4540
CGCATGAGTAACTCTCTGTTTGTGCTCTATTTTGGTTTGAATCACCATCATGATCAGCTC
ArgMetSerAsnSerLeuPheValLeuTyrPheGlyLeuAsnHisHisHisAspGlnLeu 4550      4560      4570      4580      4590      4600
GCGCATCACACGGTTTGTTTCGGCCCGCGTTACCGCGAGCTGATTGACGAAATTTTTAAT
AlaHisHisThrValCysPheGlyProArgTyrArgGluLeuIleAspGluIlePheAsn 4610      4620      4630      4640      4650      4660
CATGATGGCCTCGCAGAGGACTTCTCACTTTATCTGCACGCGCCCTGTGTCACGGATTCG
HisAspGlyLeuAlaGluAspPheSerLeuTyrLeuHisAlaProCysValThrAspSer 4670      4680      4690      4700      4710      4720
TCACTGGCGCCTGAAGGTTGCGGCAGTTACTATGTGTTGGCGCCGGTGCCGCATTTAGGC
SerLeuAlaProGluGlyCysGlySerTyrTyrValLeuAlaProValProHisLeuGly 4730      4740      4750      4760      4770      4780
ACCGCGAACCTCGACTGGACGGTTGAGGGGCCAAAACTACGCGACCGTATTTTTGCGTAC
ThrAlaAsnLeuAspTrpThrValGluGlyProLysLeuArgAspArgIlePheAlaTyr 4790      4800      4810      4820      4830      4840
CTTGAGCAGCATTACATGCCTGGCTTACGGAGTCAGCTGGTCACGCACCGGATGTTTACG
LeuGluGlnHisTyrMetProGlyLeuArgSerGlnLeuValThrHisArgMetPheThr 4850      4860      4870      4880      4890      4900
CCGTTTGATTTTCGCGACCAGCTTAATGCCTATCATGGCTCAGCCTTTTCTGTGGAGCCC
ProPheAspPheArgAspGlnLeuAsnAlaTyrHisGlySerAlaPheSerValGluPro
```

FIG. 4 (b)

```
      4910       4920       4930       4940       4950       4960
GTTCTTACCCAGAGCGCCTGGTTTCGGCCGCATAACCGCGATAAAACCATTACTAATCTC
ValLeuThrGlnSerAlaTrpPheArgProHisAsnArgAspLysThrIleThrAsnLeu 4970       4980       4990       5000       5010       5020
TACCTGGTCGGCGCAGGCACGCATCCCGGCGCAGGCATTCCTGGCGTCATCGGCTCGGCA
TyrLeuValGlyAlaGlyThrHisProGlyAlaGlyIleProGlyValIleGlySerAla 5030       5040       5050       5060
AAAGCGACAGCAGGTTTGATGCTGGAGGATCTGATTTGA
LysAlaThrAlaGlyLeuMetLeuGluAspLeuIle***
                                   ↑
                                   H
```

FIG. 4 (c)

```
      5100      5110      5120      5130      5140      5150
     ATGGCAGTTGGCTCGAAAAGTTTTGCGACAGCCTCAAAGTTATTTGATGCAAAAACCCGG
     MetAlaValGlySerLysSerPheAlaThrAlaSerLysLeuPheAspAlaLysThrArg 5160      5170      5180      5190      5200      5210
     CGCAGCGTACTGATGCTCTACGCCTGGTGCCGCCATTGTGACGATGTTATTGACGATCAG
     ArgSerValLeuMetLeuTyrAlaTrpCysArgHisCysAspAspValIleAspAspGln 5220      5230      5240      5250      5260      5270
     ACGCTGGGCTTTCAGGCCCGGCAGCCTGCCTTACAAACGCCCGAACAACGTCTGATGCAA
     ThrLeuGlyPheGlnAlaArgGlnProAlaLeuGlnThrProGluGlnArgLeuMetGln 5280      5290      5300      5310      5320      5330
     CTTGAGATGAAAACGCGCCAGGCCTATGCAGGATCGCAGATGCACGAACCGGCGTTTGCG
     LeuGluMetLysThrArgGlnAlaTyrAlaGlySerGlnMetHisGluProAlaPheAla 5340      5350      5360      5370      5380      5390
     GCTTTTCAGGAAGTGGCTATGGCTCATGATATCGCCCCGGCTTACGCGTTTGATCATCTG
     AlaPheGlnGluValAlaMetAlaHisAspIleAlaProAlaTyrAlaPheAspHisLeu 5400      5410      5420      5430      5440      5450
     GAAGGCTTCGCCATGGATGTACGCGAAGCGCAATACAGCCAACTGGATGATACGCTGCGC
     GluGlyPheAlaMetAspValArgGluAlaGlnTyrSerGlnLeuAspAspThrLeuArg 5460      5470      5480      5490      5500      5510
     TATTGCTATCACGTTGCAGGCGTTGTCGGCTTGATGATGGCGCAAATCATGGGCGTGCGG
     TyrCysTyrHisValAlaGlyValValGlyLeuMetMetAlaGlnIleMetGlyValArg 5520      5530      5540      5550      5560      5570
     GATAACGCCACGCTGGACCGCGCCTGTGACCTTGGGCTGGCATTTCAGTTGACCAATATT
     AspAsnAlaThrLeuAspArgAlaCysAspLeuGlyLeuAlaPheGlnLeuThrAsnIle 5580      5590      5600      5610      5620      5630
     GCTCGCGATATTGTGGACGATGCGCATGCGGGCCGCTGTTATCTGCCGGCAAGCTGGCTG
     AlaArgAspIleValAspAspAlaHisAlaGlyArgCysTyrLeuProAlaSerTrpLeu 5640      5650      5660      5670      5680      5690
     GAGCATGAAGGTCTGAACAAAGAGAATTATGCGGCACCTGAAAACCGTCAGGCGCTGAGC
     GluHisGluGlyLeuAsnLysGluAsnTyrAlaAlaProGluAsnArgGlnAlaLeuSer 5700      5710      5720      5730      5740      5750
     CGTATCGCCCGTCGTTTGGTGCAGGAAGCAGAACCTTACTATTTGTCTGCCACAGCCGGC
     ArgIleAlaArgArgLeuValGlnGluAlaGluProTyrTyrLeuSerAlaThrAlaGly
```

FIG. 5 (a)

```
    5760      5770      5780      5790      5800      5810
CTGGCAGGGTTGCCCCTGCGTTCCGCCTGGGCAATCGCTACGGCGAAGCAGGTTTACCGG
LeuAlaGlyLeuProLeuArgSerAlaTrpAlaIleAlaThrAlaLysGlnValTyrArg 5820      5830      5840      5850      5860      5870
AAAATAGGTGTCAAAGTTGAACAGGCCGGTCAGCAAGCCTGGGATCAGCGGCAGTCAACG
LysIleGlyValLysValGluGlnAlaGlyGlnGlnAlaTrpAspGlnArgGlnSerThr 5880      5890      5900      5910      5920      5930
ACCACGCCCGAAAAATTAACGCTGCTGCTGGCCGCCTCTGGTCAGGCCCTTACTTCCCGG
ThrThrProGluLysLeuThrLeuLeuLeuAlaAlaSerGlyGlnAlaLeuThrSerArg 5940      5950      5960      5970      5980
ATGCGGGCTCATCCTCCCCGCCCTGCGCATCTCTGGCAGCGCCCGCTCTAG
MetArgAlaHisProProArgProAlaHisLeuTrpGlnArgProLeu***
                                                ↑
                                                J
```

FIG. 5 (b)

6452
ATGTTGTGGATTTGGAATGCCCTGATCGTTTTCGTTCCGTGATTGGCATGGAAGTGATT
MetLeuTrpIleTrpAsnAlaLeuIleValPheValThrValIleGlyMetGluValIle
↑
K

GCTGCACTGGCACACAAATACATCATGCACGGCTGGGGTTGGGGATGGCATCTTTCACAT
AlaAlaLeuAlaHisLysTyrIleMetHisGlyTrpGlyTrpGlyTrpHisLeuSerHis

CATGAACCGCGTAAAGGTGCGTTTGAAGTTAACGATCTTTATGCCGTGGTTTTTGCTGCA
HisGluProArgLysGlyAlaPheGluValAsnAspLeuTyrAlaValValPheAlaAla

TTATCGATCCTGCTGATTTATCTGGGCAGTACAGGAATGTGGCCGCTCCAGTGGATTGGC
LeuSerIleLeuLeuIleTyrLeuGlySerThrGlyMetTrpProLeuGlnTrpIleGly

GCAGGTATGACGGCGTATGGATTACTCTATTTTATGGTGCACGACGGGCTGGTGCATCAA
AlaGlyMetThrAlaTyrGlyLeuLeuTyrPheMetValHisAspGlyLeuValHisGln

CGTTGGCCATTCCGCTATATTCCACGCAAGGGCTACCTCAAACGGTTGTATATGGCGCAC
ArgTrpProPheArgTyrIleProArgLysGlyTyrLeuLysArgLeuTyrMetAlaHis

CGTATGCATCACGCCGTCAGGGGCAAAGAAGGTTGTGTTTCTTTTGGCTTCCTCTATGCG
ArgMetHisHisAlaValArgGlyLysGluGlyCysValSerPheGlyPheLeuTyrAla

CCGCCCCTGTCAAAACTTCAGGCGACGCTCCGGGAAAGACATGGCGCTAGAGCGGGCGCT
ProProLeuSerLysLeuGlnAlaThrLeuArgGluArgHisGlyAlaArgAlaGlyAla

5925
GCCAGAGATGCGCAGGGCGGGGAGGATGAGCCCGCATCCGGGAAGTAA
AlaArgAspAlaGlnGlyGlyGluAspGluProAlaSerGlyLys***
                                            ↑
                                            L

FIG. 6

```
  1         10         20         30         40         50
GGTACCGCAC GGTCTGCCAA TCCGACGGAG GTTTATGAAT TTTCCACCTT TTCCACAAGC 70         80         90        100        110
         TCAACTAGTA TTAACGATGT GGATTTAGCA AAAAAAACCT GTAACCCTAA ATGTAAAATA 130        140        150        160        170
         ACGGGTAAGC CTGCCAACCA TGTTATGGCA GATTAAGCGT CTTTTTGAAG GGCACCGCAT 190        200        210        220    A  230
         CTTTCGCGTT GCCGTAAATG TATCCGTTTA TAAGGACAGC CCGAATGACG GTCTGCGCAA 250        260        270        280        290
         AAAAACACGT TCATCTCACT CGCGATGCTG CGGAGCAGTT ACTGGCTGAT ATTGATCGAC 310        320        330        340        350
         GCCTTGATCA GTTATTGCCC GTGGAGGGAG AACGGGATGT TGTGGGTGCC GCGATGCGTG 370        380        390        400        410
         AAGGTGCGCT GGCACCGGGA AAACGTATTC GCCCCATGTT GCTGTTGCTG ACCGCCCGCG 430        440        450        460        470
         ATCTGGGTTG CGCTGTCAGC CATGACGGAT TACTGGATTT GGCCTGTGCG GTGGAAATGG

490     '  500        510        520        530
         TCCACGCGGC TTCGCTGATC CTTGACGATA TGCCCTGCAT GGACGATGCG AAGCTGCGGC 550        560        570        580        590
         GCGGACGCCC TACCATTCAT TCTCATTACG GAGAGCATGT GGCAATACTG GCGGCGGTTG 610        620        630        640        650
         CCTTGCTGAG TAAAGCCTTT GGCGTAATTG CCGATGCAGA TGGCCTCACG CCGCTGGCAA

.670       680        690        700        710
         AAAATCGGGC GGTTTCTGAA CTGTCAAACG CCATCGGCAT GCAAGGATTG GTTCAGGGTC 730        740        750        760        770
         AGTTCAAGGA TCTGTCTGAA GGGGATAAGC CGCGCAGCGC TGAAGCTATT TTGATGACGA 790        800        810        820        830
         ATCACTTTAA AACCAGCACG CTGTTTTGTG CCTCCATGCA GATGGCCTCG ATTGTTGCGA 850        860        870        880        890
         ATGCCTCCAG CGAAGCGCGT GATTGCCTGC ATCGTTTTTC ACTTGATCTT GGTCAGGCAT 910        920        930        940        950
         TTCAACTGCT GGACGATTTG ACCGATGGCA TGACCGACAC CGGTAAGGAT AGCAATCAGG 970        980        990       1000       1010
         ACGCCGGTAA ATCGACGCTG GTCAATCTGT TAGGCCCGAG GGCGGTTGAA GAACGTCTGA 1030       1040       1050       1060       1070
         GACAACATCT TCAGCTTGCC AGTGAGCATC TCTCTGCGGC CTGCCAACAC GGGCACGCCA 1090       1100       1110       1120       1130 B
         CTCAACATTT TATTCAGGCC TGGTTTGACA AAAAACTCGC TGCCGTCAGT TAAGGATGCT
```

FIG. 7 (a)

```
     C   1150        1160       1170       1180       1190
     ↓
   GCATGAGCCA  TTTCGCGGCG  ATCGCACCGC  CTTTTTACAG  CCATGTTCGC  GCATTACAGA 1210        1220       1230       1240       1250
   ATCTCGCTCA  GGAACTGGTC  GCGCGCGGTC  ATCGGGTGAC  CTTTATTCAG  CAATACGATA 1270        1280       1290       1300       1310
   TTAAACACTT  GATCGATAGC  GAAACCATTG  GATTTCATTC  CGTCGGGACA  GACAGCCATC 1330        1340       1350       1360       1370
   CCCCCGGCGC  GTTAACGCGC  GTGCTACACC  TGGCGGCTCA  TCCTCTGGGG  CCGTCAATGC 1390        1400       1410       1420       1430
   TGAAGCTCAT  CAATGAAATG  GCGCGCACCA  CCGATATGCT  GTGCCGCGAA  CTCCCCCAGG 1450        1460       1470       1480       1490
   CATTTAACGA  TCTGGCCGTC  GATGGCGTCA  TTGTTGATCA  AATGGAACCG  GCAGGCGCGC 1510        1520       1530       1540       1550
   TCGTTGCTGA  AGCACTGGGA  CTGCCGTTTA  TCTCTGTCGC  CTGCGCGCTG  CCTCTCAATC 1570        1580       1590       1600       1610
   GTGAACCGGA  TATGCCCCTG  GCGGTTATGC  CTTTCGAATA  CGGGACCAGC  GACGCGGCTC 1630        1640       1650       1660       1670
   GCGAACGTTA  TGCCGCCAGT  GAAAAAATTT  ATGACTGGCT  AATGCGTCGT  CATGACCGTG 1690        1700       1710       1720       1730
   TCATTGCCGA  ACACAGCCAC  AGAATGGGCT  TAGCCCCCCG  GCAAAAGCTT  CACCAGTGTT 1750        1760       1770       1780       1790
   TTTCGCCACT  GGCGCAAATC  AGCCAGCTTG  TTCCTGAACT  GGATTTTCCC  CGCAAAGCGT 1810        1820       1830       1840       1850
   TACCGGCTTG  TTTTCATGCC  GTCGGGCCTC  TGCGCGAAAC  GCACGCACCG  TCAACGTCTT 1870        1880       1890       1900       1910
   CATCCCGTTA  TTTTACATCC  TCAGAAAAAC  CCCGGATTTT  CGCCTCGCTG  GGCACGCTTC 1930        1940       1950       1960       1970
   AGGGACACCG  TTATGGGCTG  TTTAAAACGA  TAGTGAAAGC  CTGTGAAGAA  ATTGACGGTC 1990        2000       2010       2020       2030
   AGCTCCTGTT  AGCCCACTGT  GGTCGTCTTA  CGGACTCTCA  GTGTGAAGAG  CTGGCGCGAA 2050        2060       2070       2080       2090
   GCCGTCATAC  ACAGGTGGTG  GATTTTGCCG  ATCAGTCAGC  CGCGCTGTCT  CAGGCGCAGC 2110        2120       2130       2140       2150
   TGGCGATCAC  CCACGGCGGC  ATGAATACGG  TACTGGACGC  GATTAATTAC  CGGACGCCCC 2170        2180       2190       2200       2210
   TTTTAGCGCT  TCCGCTGGCC  TTTGATCAGC  CCGGCGTCGC  GTCACGCATC  GTTTATCACG 2230        2240       2250       2260       2270
   GCATCGGCAA  GCGTGCTTCC  CGCTTTACCA  CCAGCCATGC  TTTGGCTCGT  CAGATGCGTT
```

FIG. 7 (b)

```
         2290       2300       2310       2320       2330
    CATTGCTGAC CAACGTCGAC TTTCAGCAGC GCATGGCGAA AATCCAGACA GCCCTTCGTT 2350       2360       2370       2380       2390
    TGGCAGGGGG CACCATGGCC GCTGCCGATA TCATTGAGCA GGTTATGTGC ACCGGTCAGC 2410       2420  E  2430     D 2440       2450
    CTGTCTTAAG TGGGAGCGGC TATGCAACCG CATTATGATC TGATTCTCGT GGGGGCTGGA 2470       2480       2490       2500       2510
    CTCGCGAATG GCCTTATCGC CCTGCGTCTT CAGCAGCAGC AACCTGATAT GCGTATTTTG 2530       2540       2550       2560       2570
    CTTATCGACG CCGCACCCCA GGCGGGCGGG AATCATACGT GGTCATTTCA CCACGATGAT 2590       2600       2610       2620       2630
    TTGACTGAGA GCCAACATCG TTGGATAGCT CCGCTGGTGG TTCATCACTG GCCCGACTAT 2650       2660       2670       2680       2690
    CAGGTACGCT TTCCCACACG CCGTCGTAAG CTGAACAGCG GCTACTTTTG TATTACTTCT 2710       2720       2730       2740       2750
    CAGCGTTTCG CTGAGGTTTT ACAGCGACAG TTTGGCCCGC ACTTGTGGAT GGATACCGCG 2770       2780       2790       2800       2810
    GTCGCAGAGG TTAATGCGGA ATCTGTTCGG TTGAAAAAGG GTCAGGTTAT CGGTGCCCGC 2830       2840       2850       2860       2870
    GCGGTGATTG ACGGGCGGGG TTATGCGGCA AATTCAGCAC TGAGCGTGGG CTTCCAGGCG 2890       2900       2910       2920       2930
    TTTATTGGCC AGGAATGGCG ATTGAGCCAC CCGCATGGTT TATCGTCTCC CATTATCATG 2950       2960       2970       2980       2990
    GATGCCACGG TCGATCAGCA AAATGGTTAT CGCTTCGTGT ACAGCCTGCC GCTCTCGCCG 3010       3020       3030       3040       3050
    ACCAGATTGT TAATTGAAGA CACGCACTAT ATTGATAATG CGACATTAGA TCCTGAATGC 3070       3080       3090       3100       3110
    GCGCGGCAAA ATATTTGCGA CTATGCCGCG CAACAGGGTT GGCAGCTTCA GACACTGCTG 3130       3140       3150       3160       3170
    CGAGAAGAAC AGGGCGCCTT ACCCATTACT CTGTCGGGCA ATGCCGACGC ATTCTGGCAG 3190       3200       3210       3220       3230
    CAGCGCCCCC TGGCCTGTAG TGGATTACGT GCCGGTCTGT TCCATCCTAC CACCGGCTAT 3250       3260       3270       3280       3290
    TCACTGCCGC TGGCGGTTGC CGTGGCCGAC CGCCTGAGTG CACTTGATGT CTTTACGTCG 3310       3320       3330       3340       3350
    GCCTCAATTC ACCATGCCAT TACGCATTTT GCCCGCGAGC GCTGGCAGCA GCAGGGCTTT 3370       3380       3390       3400       3410
    TTCCGCATGC TGAATCGCAT GCTGTTTTTA GCCGGACCCG CCGATTCACG CTGGCGGGTT
```

FIG. 7 (c)

```
      3430         3440         3450         3460         3470
ATGCAGCGTT   TTTATGGTTT   ACCTGAAGAT   TTAATTGCCC   GTTTTTATGC   GGGAAAACTC 3490         3500         3510         3520         3530
ACGCTGACCG   ATCGGCTACG   TATTCTGAGC   GGCAAGCCGC   CTGTTCCGGT   ATTAGCAGCA
                                    F                        G
      3550         3560         3570         3580         3590
TTGCAAGCCA   TTATGACGAC   TCATCGTTAA   AGAGCGACTA   CATGAAACCA   ACTACGGTAA 3610         3620         3630         3640         3650
TTGGTGCAGG   CTTCGGTGGC   CTGGCACTGG   CAATTCGTCT   ACAAGCTGCG   GGGATCCCCG 3670         3680         3690         3700         3710
TCTTACTGCT   TGAACAACGT   GATAAACCCG   GCGGTCGGGC   TTATGTCTAC   GAGGATCAGG 3730         3740         3750         3760         3770
GGTTTACCTT   TGATGCAGGC   CCGACGGTTA   TCACCGATCC   CAGTGCCATT   GAAGAACTGT 3790         3800         3810         3820         3830
TTGCACTGGC   AGGAAAACAG   TTAAAGAGT   ATGTCGAACT   GCTGCCGGTT   ACGCCGTTTT 3850         3860         3870         3880         3890
ACCGCCTGTG   TTGGGAGTCA   GGGAAGGTCT   TTAATTACGA   TAACGATCAA   ACCCGGCTCG 3910         3920         3930         3940         3950
AAGCGCAGAT   TCAGCAGTTT   AATCCCCGCG   ATGTCGAAGG   TTATCGTCAG   TTTCTGGACT 3970         3980         3990         4000         4010
ATTCACGCGC   GGTGTTTAAA   GAAGGCTATC   TAAAGCTCGG   TACTGTCCCT   TTTTTATCGT 4030         4040         4050         4060         4070
TCAGAGACAT   GCTTCGCGCC   GCACCTCAAC   TGGCGAAACT   GCAGGCATGG   AGAAGCGTTT 4090         4100         4110         4120         4130
ACAGTAAGGT   TGCCAGTTAC   ATCGAAGATG   AACATCTGCG   CCAGGCGTTT   TCTTTCCACT 4150         4160         4170         4180         4190
CGCTGTTGGT   GGGCGGCAAT   CCCTTCGCCA   CCTCATCCAT   TTATACGTTG   ATACACGCGC 4210         4220         4230         4240         4250
TGGAGCGTGA   GTGGGCGTC   TGGTTTCCGC   GTGGCGGCAC   CGGCGCATTA   GTTCAGGGGA 4270         4280         4290         4300         4310
TGATAAAGCT   GTTTCAGGAT   CTGGGTGGCG   AAGTCGTGTT   AAACGCCAGA   GTCAGCCATA 4330         4340         4350         4360         4370
TGGAAACGAC   AGGAAACAAG   ATTGAAGCCG   TGCATTTAGA   GGACGGTCGC   AGGTTCCTGA 4390         4400         4410         4420         4430
CGCAAGCCGT   CGCGTCAAAT   GCAGATGTGG   TTCATACCTA   TCGCGACCTG   TTAAGCCAGC 4450         4460         4470         4480         4490
ACCCTGCCGC   GGTTAAGCAG   TCCAACAAAC   TGCAGACTAA   GCGCATGAGT   AACTCTCTGT 4510         4520         4530         4540         4550
TTGTGCTCTA   TTTTGGTTTG   AATCACCATC   ATGATCAGCT   CGCGCATCAC   ACGGTTTGTT
```

FIG. 7 (d)

```
      4570       4580       4590       4600       4610
TCGGCCCGCG TTACCGCGAG CTGATTGACG AAATTTTTAA TCATGATGGC CTCGCAGAGG 4630       4640       4650       4660       4670
ACTTCTCACT TTATCTGCAC GCGCCCTGTG TCACGGATTC GTCACTGGCG CCTGAAGGTT 4690       4700       4710       4720       4730
GCGGCAGTTA CTATGTGTTG GCGCCGGTGC CGCATTTAGG CACCGCGAAC CTCGACTGGA 4750       4760       4770       4780       4790
CGGTTGAGGG GCCAAAACTA CGCGACCGTA TTTTTGCGTA CCTTGAGCAG CATTACATGC 4810       4820       4830       4840       4850
CTGGCTTACG GAGTCAGCTG GTCACGCACC GGATGTTTAC GCCGTTTGAT TTTCGCGACC 4870       4880       4890       4900       4910
AGCTTAATGC CTATCATGGC TCAGCCTTTT CTGTGGAGCC CGTTCTTACC CAGAGCGCCT 4930       4940       4950       4960       4970
GGTTTCGGCC GCATAACCGC GATAAAACCA TTACTAATCT CTACCTGGTC GGCGCAGGCA 4990       5000       5010       5020       5030
CGCATCCCGG CGCAGGCATT CCTGGCGTCA TCGGCTCGGC AAAAGCGACA GCAGGTTTGA
                 H
      5050       5060       5070       5080       5090
TGCTGGAGGA TCTGATTTGA ATAATCCGTC GTTACTCAAT CATGCGGTCG AAACGATGGC 5110       5120       5130       5140       5150
AGTTGGCTCG AAAAGTTTTG CGACAGCCTC AAAGTTATTT GATGCAAAAA CCCGGCGCAG 5170       5180       5190       5200       5210
CGTACTGATG CTCTACGCCT GGTGCCGCCA TTGTGACGAT GTTATTGACG ATCAGACGCT 5230       5240       5250       5260       5270
GGGCTTTCAG GCCCGGCAGC CTGCCTTACA AACGCCCGAA CAACGTCTGA TGCAACTTGA 5290       5300       5310       5320       5330
GATGAAAACG CGCCAGGCCT ATGCAGGATC GCAGATGCAC GAACCGGCGT TTGCGGCTTT 5350       5360       5370       5380       5390
TCAGGAAGTG GCTATGGCTC ATGATATCGC CCCGGCTTAC GCGTTTGATC ATCTGGAAGG 5410       5420       5430       5440       5450
CTTCGCCATG GATGTACGCG AAGCGCAATA CAGCCAACTG GATGATACGC TGCGCTATTG 5470       5480       5490       5500       5510
CTATCACGTT GCAGGCGTTG TCGGCTTGAT GATGGCGCAA ATCATGGGCG TGCGGGATAA 5530       5540       5550       5560       5570
CGCCACGCTG GACCGCGCCT GTGACCTTGG GCTGGCATTT CAGTTGACCA ATATTGCTCG 5590       5600       5610       5620       5630
CGATATTGTG GACGATGCGC ATGCGGGCCG CTGTTATCTG CCGGCAAGCT GGCTGGAGCA 5650       5660       5670       5680       5690
TGAAGGTCTG AACAAAGAGA ATTATGCGGC ACCTGAAAAC CGTCAGGCGC TGAGCCGTAT
```

FIG. 7 (e)

```
       5710       5720       5730       5740       5750
CGCCCGTCGT TTGGTGCAGG AAGCAGAACC TTACTATTTG TCTGCCACAG CCGGCCTGGC 5770       5780       5790       5800       5810
AGGGTTGCCC CTGCGTTCCG CCTGGGCAAT CGCTACGGCG AAGCAGGTTT ACCGGAAAAT 5830       5840       5850       5860       5870
AGGTGTCAAA GTTGAACAGG CCGGTCAGCA AGCCTGGGAT CAGCGGCAGT CAACGACCAC
                                                    L
       5890       5900       5910       5920       5930
GCCCGAAAAA TTAACGCTGC TGCTGGCCGC CTCTGGTCAG GCCCTTACTT CCCGGATGCG
                                                 J
       5950       5960       5970       5980       5990
GGCTCATCCT CCCCGCCCTG CGCATCTCTG GCAGCGCCCG CTCTAGCGCC ATGTCTTTCC 6010       6020       6030       6040       6050
CGGAGCGTCG CCTGAAGTTT TGACAGGGGC GGCGCATAGA GGAAGCCAAA AGAAACACAA 6070       6080       6090       6100       6110
CCTTCTTTGC CCCTGACGGC GTGATGCATA CGGTGCGCCA TATACAACCG TTTGAGGTAG 6130       6140       6150       6160       6170
CCCTTGCGTG GAATATAGCG GAATGGCCAA CGTTGATGCA CCAGCCCGTC GTGCACCATA 6190       6200       6210       6220       6230
AAATAGAGTA ATCCATACGC CGTCATACCT GCGCCAATCC ACTGGAGCGG CCACATTCCT 6250       6260       6270       6280       6290
GTACTGCCCA GATAAATCAG CAGGATCGAT AATGCAGCAA AAACCACGGC ATAAAGATCG 6310       6320       6330       6340       6350
TTAACTTCAA ACGCACCTTT ACGCGGTTCA TGATGTGAAA GATGCCATCC CCAACCCCAG 6370       6380       6390       6400       6410
CCGTGCATGA TGTATTTGTG TGCCAGTGCA GCAATCACTT CCATGCCAAT CACGGTAACG
                              K
       6430       6440       6450       6460       6470
AAAACGATCA GGGCATTCCA AATCCACAAC ATAATTTCTC CGGTAGAGAC GTCTGGCAGC 6490       6500       6510       6520       6530
AGGCTTAAGG ATTCAATTTT AACAGAGATT AGCCGATCTG GCGGCGGGAA GGGAAAAAGG 6550       6560       6570       6580       6590
CGCGCCAGAA AGGCGCGCCA GGGATCAGAA GTCGGCTTTC AGAACCACAC GGTAGTTGGC 6610       6620       6630       6640       6650
TTTACCTGCA CGAACATGGT CCAGTGCATC GTTGATTTTC GACATCGGGA AGTACTCCAC 6670       6680       6690       6700       6710
TGTCGGCGCA ATATCTGTAC GGCCAGCCAG CTTCAGCAGT GAACGCAGCT GCGCAGGTGA 6730       6740       6750       6760       6770
ACCGGTTGAA GAACCCGTCA CGGCGCGGTC GCCTAAAATC AGGCTGAAAG CCGGGCACGT 6790       6800       6810       6820       6830
CAAACGGCTT CAGTACGGCA CCCACGGTAT GGAACTTACC GCGAGGCGCC AGGGCCGCAA
```

FIG. 7 (f)

```
        6850       6860       6870       6880       6890
AGTAGGGTTG CCAGTCGAGA TCGACGGCGA CCGTGCTGAT AATCAGGTCA AACTGGCCCG 6910     6918
CCAGGCTTTT TAAAGCTT
```

FIG. 7 (g)

DNA SEQUENCES USEFUL FOR THE SYNTHESIS OF CAROTENOIDS

This is a continuation of copending U.S. patent application Ser. No. 07/519,011 filed on Apr. 19, 1990, abandoned.

BACKGROUND OF THE INVENTION

1. Field of the Art

The present invention relates to DNA sequences which are useful for the synthesis of carotenoids such as lycopene, β-carotene, zeaxanthin or zeaxanthin-diglucoside.

The present invention also relates to processes for producing such carotenoid compounds.

2. Related Art

Carotenoids are distributed widely in green plants. They are yellow-orange-red lipids which are also present in some mold, yeast and so forth, and have recently received increased attention as natural coloring materials for foods. Among these carotenoids, β-carotene is a typical one, which is used as a coloring materials and as a precursor of vitamin A in mammals as well. It is also examined for its use as a component for preventing cancer [see, for example, SHOKUHIN TO KAIHATSU (Foods and Development), 24, 61–65 (1989)]. Carotenoids such as β-carotene are widely distributed in green plants, so that the plant tissue culture has been examined for the development of a method for producing carotenoids in a large amount which is free from the influence of natural environment [see, for example, Plant Cell Physiol., 12, 525–531 (1971)]. The examination has been also made for detecting a microorganism such as mold, yeast or green algae which is originally high carotenoid productive and for producing carotenoids in a large amount with use of such microorganism (see, for example, The Abstract of Reports in the Annual Meeting of NIPPON HAKKO KOGAKU-KAI of 1988, page 139). However, neither of these methods are successful at present in producing β-carotene at a good productivity which exceeds the synthetic method in commercial production of β-carotene. It would be very useful to obtain a gene group which participates in the biosynthesis of carotenoids, because it will be possible to produce carotenoids in a large amount by introducing a gene group which has been reconstructed to express proper genes in the gene group in a large amount, into an appropriate host such as a plant tissue culture cell, a mold, an yeast or the like which originally produces carotenoids. Such a development in technology has possibilities for finding a method of producing β-carotene superior to the synthetic method and a method of producing useful carotenoids other than β-carotene in a large amount.

Furthermore, the synthesis of carotenoids in a cell or an organ which produces no carotenoid will be possible by obtaining the gene group participating in the biosynthesis of carotenoids, which will add new values to organisms. For example, several reports have recently been made with reference to creating flower colors which cannot be found in nature by using genetic manipulation in flowering plants [see, for example, Nature, 330, 677–678 (1987)]. The color of flowers is developed by pigments such as anthocyanine or carotenoids. Anthocyanine is responsible for flower colors in the spectrum of red-violet-blue, and carotenoids are responsible for flower colors in the spectrum of yellow-orange-red. The gene of the enzyme for synthesizing anthocyanine has been elucidated, and the aforementioned reports for creating a new flower color are those referring to anthocyanine. On the other hand, there are many flowering plants having no bright yellow flower due to no function of synthesizing carotenoids in petal (e.g. petunia, saintpaulia (african violet), cyclamen, Primula malacoides, etc.). If suitable genes having been reconstructed so as to be expressed in petal in a gene group referring to the biosynthesis of carotenoids are introduced into these flowering plants, the flowering plants having yellow flowers will be created successfully.

However, enzymes for synthesizing carotenoids or genes coding for them have been scarcely elucidated at present. The nucleotide sequence of the gene group participating in the biosynthesis of a kind of carotenoids has been elucidated lately only in a photosynthetic bacterium *Rhodobacter capsulatus* [Mol. Gen. Genet., 216, 254–268 (1989)]. But this bacterium synthesizes the acyclic xanthophyll spheroidene via neurosporene without cyclization and thus cannot synthesize general carotenoids such as lycopene, β-carotene and zeaxanthin.

There are prior arts with reference to yellow pigments or carotenoids of Erwinia species disclosed in J. Bacteriol., 168, 607–612 (1986), J. Bacteriol., 170, 4675–4680 (1988) and J. Gen. Microbiol., 130, 1623–1631 (1984). The first one of these references discloses the cloning of a gene cluster coding for yellow pigment synthesis from Erwinia herbicola Eho 10 ATCC 39368 as a 12.4 kilobase pair (kb) fragment. In this connection, there is no illustration of the nucleotide sequence of the 12.4 kb fragment. The second literature discloses the yellow pigment synthesized by the cloned gene cluster, which is indicated to belong to carotenoids by the analysis of its UV-visible spectrum. The last literature indicates that the gene participating in the production of a yellow pigment is present in a 260 kb large plasmid contained in *Erwinia uredovora* 20D3 ATTC 19321 from the observation that the yellow pigment is not produced on curing the large plasmid, and further discloses that the pigment belongs to carotenoids from the analysis of its UV-visible spectrum.

However, the chemical structures of carotenoids produced by the Erwinia species or of its metabolic intermediates, enzymes participating in the synthesis of them or the nucleotide sequence of the genes encoding these enzymes remain unknown at present.

DISCLOSURE OF THE INVENTION

BRIEF DESCRIPTION OF THE FIGURES

FIGS. 1(a), 1(b), 2(a), 2(b), 3(a), 3(b), 4(a), 4(b), 4(c), 5(a), 5(b), 6,7(a), 7(b), 7(c), 7(d), 7(e), 7(f), 7(f), and 7(g) are the sequences of the DNA encoding the enzymes for the conversion carotenoids.

OUTLINE OF THE INVENTION

Figure 8:
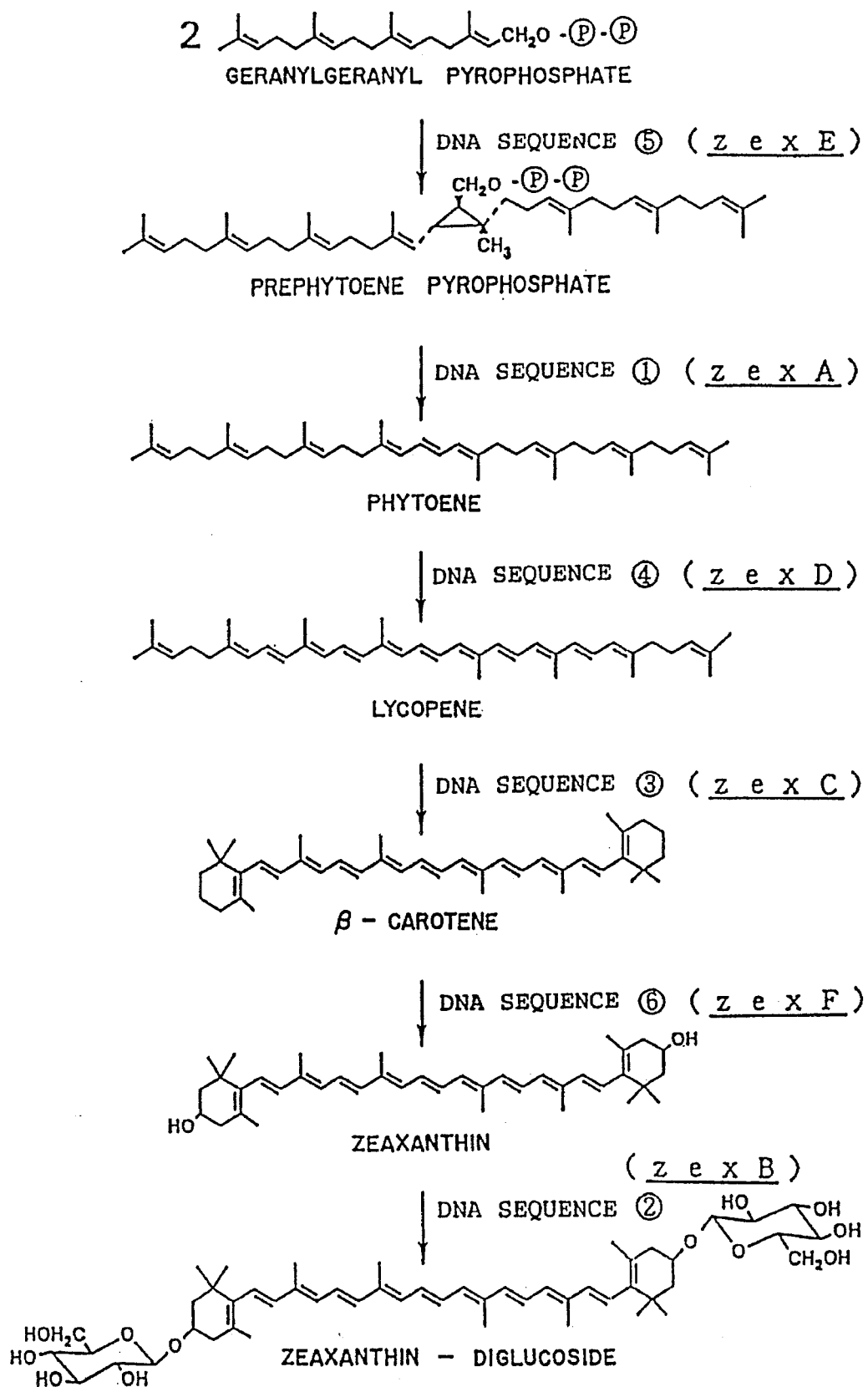
FIG. 8 depicts the pathway for the conversion.

The object of the present invention is to provide DNA sequences which are useful for the synthesis of carotenoids such as lycopene, β-carotene, zeaxanthin or zeaxanthin-diglucoside, that is DNA sequences encoding carotenoid biosynthesis enzymes.

In other words, the DNA sequences useful for the synthesis of carotenoids according to the present invention are the DNA sequences ①–⑥ described in the following (1)–(6).

(1) a DNA sequence encoding a polypeptide which is enzymatically active in carotenoid biosynthesis farnesyl pyrophosphate into geranylgeranyl pyrophosphate and whose amino acid sequence corresponds substantially to the amino acid sequence from A to B shown in FIGS. 1-(a) and (b) (DNA sequence ①);

(2) a DNA sequence encoding a polypeptide which has an enzymatic activity for converting zeaxanthin into β-carotene zeaxanthin-diglucoside and whose amino acid sequence corresponds substantially to the amino acid sequence from C to D shown in FIGS. 2-(a) and (b) (DNA sequence ②);

(3) a DNA sequence encoding a polypeptide which has an enzymatic activity for converting lycopene into carotene and whose amino acid sequence corresponds substantially to the amino acid sequence from E to F shown in FIGS. 3-(a) and (b) (DNA sequence ③);

(4) a DNA sequence encoding a polypeptide which has an enzymatic activity for converting phytoene into lycopene and whose amino acid sequence corresponds substantially to the amino acid sequence from G to H shown in FIGS. 4-(a), (b) and (c) (DNA sequence ④);

(5) a DNA sequence encoding a polypeptide which has an enzymatic activity for converting geranylgeranyl pyrophosphate into product and whose amino acid sequence corresponds substantially to the amino acid sequence from I to J shown in FIGS. 5-(a) and (b) (DNA sequence ⑤); and (6) a DNA sequence encoding a polypeptide which has an enzymatic activity for converting β-carotene into zeaxanthin and whose amino acid sequence corresponds substantially to the amino acid sequence from K to L shown in FIG. 6 (DNA sequence ⑥).

Another object of the present invention is to provide processes for producing carotenoid compounds.

More specifically, the present invention also provides a process for producing a carotenoid compound which is related from the group consisting of prephytoene pyrophosphate, phytoene, lycopene, β-carotene, zeaxanthin and zeaxanthin-diglucoside, which comprises transforming a host with at least one of DNA sequences ①–⑥ described above and culturing the transformant.

EFFECT OF THE INVENTION

The successful acquirement of the gene group (gene group encoding the biosynthetic enzymes of carotenoids) useful for the synthesis of carotenoids such as lycopene, β-carotene, zeaxanthin, zeaxanthin-diglucoside or the like according to the present invention has made it possible to produce useful carotenoids in large amounts, for example, by creating a plasmid in which the gene(s) can be expressed in a large amount and employing an appropriate plant tissue culture cell, a microorganism or the like transformed with the plasmid. The success in acquiring the gene group useful for the synthesis of carotenoids such as lycopene, β-carotene, zeaxanthin, zeaxanthin-diglucoside or the like according to the present invention has made it possible to synthesize carotenoids in cells or organs which produce no carotenoid by creating a plasmid in which the gene(s) can be expressed in a target cell or organ and transforming a suitable host with this plasmid.

DETAILED DESCRIPTION OF THE INVENTION

The DNA sequences according to the present invention are the aforementioned DNA sequences ①–⑥, that is, genes encoding the polypeptides of respective enzymes which participate in the biosynthesis reaction of carotenoids, in particular, for example, such polypeptides in *Erwinia uredovora* 20D3 ATCC 19321.

A variety of gene groups containing the DNA sequences of a combination of a plurality of sequences among these DNA sequences ①–⑥ can be expressed in a microorganism, a plant or the like to afford them the biosynthesis ability of carotenoids such as lycopene, β-carotene, zeaxanthin, zeaxanthin-diglucoside or the like. The respective DNA sequences constructing the gene group may be present on a DNA strand or on different DNA strands individually, or optionally, the respective DNA sequences may comprise a plurality of DNA sequences present on a DNA strand and a DNA sequence present on another DNA strand.

The aforementioned gene group encode the polypeptides of a plurality of enzymes participating in the production of carotenoids. A recombinant DNA is created by incorporating the gene group into a proper vector and then introduced into a suitable host to create a transformant, which is cultured to produce mainly in the transformant a plurality of enzymes participating in the formation reaction of carotenoids and to conduct the biosynthesis of carotenoids in the transformant by these enzymes.

The DNA sequence shown in FIGS. 7-(a) to (g), which is an example according to the present invention, is acquired from *Erwinia uredovora* 20D3 ATCC 19321 and thus exhibits, as illustrated in the experimental example below, no homology in the DNA-DNA hybridization with the DNA strand containing the gene group for synthesizing the yellow pigment of *Erwinia herbicola* Eho 10 ATCC 39368 (see Related Art described above).

DNA Sequences encoding the polypeptide of each enzyme

The DNA sequences of the present invention are the DNA sequences ①–⑥ (or the DNA strands ①–⑥), respectively. Each of the DNA sequences contains a nucleotide sequence encoding the polypeptide whose amino acid sequence corresponds substantially to such an amino acid sequence as in the aforementioned specific regions in FIGS. 1–6 (for example, from A to B in FIG. 1). In this connection the term "DNA sequence" means a polydeoxyribonucleic acid sequence having a length. In the present invention, the "DNA sequence" is defined by an amino acid sequence of a polypeptide which is encoded by the DNA sequence and has a definite length as described above, so that each DNA sequence has also a definite length. However, the DNA sequence contains a gene encoding each enzyme and is useful for biotechnological production of the polypeptide, and such biotechnological production cannot be performed by only the DNA sequence having a definite length but can be performed in the state where other DNA sequence with a proper length is linked to the 5'-upstream and/or the 3'-downstream of the DNA sequence. Therefore, the term "DNA sequence" in the present invention includes, in addition to those having a definite length (for example, the length in the region of A–B in the corresponding amino acid sequence of FIG. 1), those in the form of a linear DNA strand or a circular DNA strand containing the DNA sequence having a definite length as a member.

One of the typical forms of each DNA sequence according to the present invention is a form of a plasmid which comprises the DNA sequence as a part of a member or a form in which the plasmid is present in a host such as *E. coli*. The plasmid as one of the preferable existing forms of each DNA sequence according to the present invention is a conjunction of the DNA sequence according to the present invention as a passenger or a foreign gene, a replicable plasmid vector present stably in a host and a promoter (containing ribosome-binding sites in the case of a procaryote). As the plasmid vector and the promoter, an appropriate combination of those which are well-known can be used.

Polypeptides encoded by DNA sequences

As mentioned above, the DNA sequences according to the present invention are respectively specified by the amino acid sequences of the polypeptides encoded thereby. Each of these polypeptides is the one having an amino acid sequence which corresponds substantially to an amino acid sequence in a specific region as described above in FIGS. 1–6(for example, from A to B in FIG. 1). Here, in the six (A–B, C–D, E–F, G–H, I–J, K–L) polypeptides shown in FIGS. 1–6 (i.e. six enzymes participating in the formation of carotenoids), some of the amino acids can be deleted or substituted or some amino acids can be added or inserted, etc., so long as each polypeptide has the aforementioned enzymatic activity in the relationship of a substrate and a converted substance (a product). This is indicated by the expression "whose amino acid sequence corresponds substantially to . . . " in the claims. For example, each polypeptide that first amino acid (Met) has been deleted from each polypeptide shown in FIGS. 1–6 is included in such deleted polypeptides.

The typical polypeptides having enzymatic activities, respectively, in the present invention are those in the specific regions in FIGS. 1–6 described above, and the amino acid sequences of these polypeptides have not been known.

Nucleotide sequences of DNA sequences

The DNA sequences encoding the respective enzymes are those having the nucleotide sequences in the aforementioned specific regions in FIGS. 1–6 (for example, A–B in FIG. 1) or degenerative isomers thereof, or those having the nucleotide sequences corresponding to the aforementioned alteration of the amino acid sequence of respective enzymes or degenerative isomers thereof. The term "degenerative isomer" means DNA sequence which is different only in degenerative codon and can code for the same polypeptide. The preferred embodiments of the DNA sequences according to the present invention are those having at least one stop codon (such as TAA) at the 3'-terminal. The 5'-upstream and/or the 3'-downstream of the DNA sequences according to the present invention may further have a DNA sequence with a certain length as a non-translation region (the initial portion of the 3'-downstream being usually a stop codon such as TAA).

Gene group used for the synthesis of carotenoids

The gene group (the gene cluster in some case) used for the synthesis of carotenoids comprises a plurality of the aforementioned DNA sequences ①–⑥, whose typical examples are illustrated in the following (1)–(4). Each gene group encodes a plurality of polypeptides of respective enzymes and these enzymes participate in the production reaction of carotenoids to produce them from their substrates.

(1) Gene group used for the synthesis of lycopene

The gene group used for the synthesis of lycopene which is a red carotenoid is DNA sequence comprising the aforementioned DNA sequences ①, ④ and ⑤, and such a gene group includes the one in which respective DNA sequences are present on one DNA strand or on different DNA strands separately or the one which is constructed by the combination of the aforementioned ones according to necessities.

In the case that a plurality of DNA sequences are present on one DNA strand, the arrangement order and direction of the aforementioned DNA sequences ①, ④ and ⑤ may be optional provided that the genetic information is capable of expression, that is to say respective genes in a host are in a state of being transcribed and translated appropriately.

The biosynthetic pathway of lycopene in E. coli is explained as follows: geranylgeranyl pyrophosphate which is a substrate originally present in E. coli is converted into product phytoene by the enzyme encoded by the DNA sequence ⑤ and the product is converted into lycopene by the enzyme encoded by the DNA sequence ④. The enzyme encoded by the DNA sequence ① converts farnesyl pyrophosphate into geranylgeranyl pyrophosphate and thus is necessary to increase the production of lycopene.

Lycopene is a carotene whose color is red. Lycopene is a red pigment which is present in a large amount in the fruits of water melon or tomato and has high safety for food. In this connection, the lycopene which was synthesized by the DNA sequences according to the present invention in the experimental example described below had the same stereochemistry as lycopene present in these plants.

One of the typical existing forms of the gene group of the present invention is a form of a plasmid which comprises the respective DNA sequences containing a stop codon as a member or a form in which the plasmid is present in a host such as E. coli. The plasmid which is one of the preferred existing forms of the gene group according to the present invention comprises a gene group as a passenger or a foreign gene, a replicable plasmid vector present stably in a host and a promoter (containing ribosome-binding sites in the case of a procaryote). As the promoter, in procaryotes such as E. coli or Zymomonas species a promoter which is common to respective DNA sequences can be used, or alternatively respective promoters can be used to the respective DNA sequences. In the case of eucaryotes such as yeast or plant, respective promoters are preferably used to respective DNA sequences.

One of the preferred existing forms of the DNA sequences are described above in the explanation of the DNA sequences ①–⑥.

2) Gene group used for the synthesis of β-carotene

The gene group used for the synthesis of β-carotene which is one of yellow-orange carotenoids is a DNA sequence comprising the aforementioned DNA sequences ①, ③, ④ and ⑤. In other words, the gene group used for the synthesis of β-carotene is formed by adding the DNA sequence ③ to a DNA sequence used for the synthesis of lycopene comprising the DNA sequences ①, ④, and ⑤. The gene group includes the one in which the respective DNA sequences constructing the gene group may be present on one DNA strand or on different DNA strands individually, or the one which is constructed by the combination of the aforementioned ones according to necessities.

In the case that a plurality of DNA sequences are present on one DNA strand, the arrangement order and direction of the aforementioned DNA sequences ①, ③, ④ and ⑤ may be optional provided that the genetic information is capable of expression, that is to say respective genes in a host are in a state of being transcribed and translated appropriately.

The biosynthetic pathway of β-carotene in E. coli is explained as follows: geranylgeranyl pyrophosphate which is a substrate originally present in E. coli is converted into product pytoene by the enzyme encoded by the DNA sequence ⑤ and the products converted into lycopene by the enzyme encoded by the DNA sequence ④, and the lycopene is further converted into β-carotene by the enzyme encoded by the DNA sequence ③.

The enzyme encoded by the DNA sequence ① converts farnesyl pyrophosphate into geranylgeranyl pyrophosphate and thus is necessary to increase the product of β-carotene.

β-carotene is a typical carotene whose color is the spectrum ranging from yellow to orange, and it is an orange pigment which is present in a large amount in the roots of carrot or green leaves of plants and has high safety for food. The utility of β-carotene has already been described in the explanation of related art. In this connection, the β-carotene which was synthesized by the DNA sequence according to the present invention in the experimental example described below had the same stereochemistry as β-carotene present in the roots of carrot or green leaves of plants.

One of the typical existing forms of the gene group and the individual DNA sequences are the same as defined in (1).

(3) Gene group used for the synthesis of zeaxanthin

The gene group used for the synthesis of zeaxanthin which is one of yellow-orange carotenoids is a DNA sequence comprising the aforementioned DNA sequences ①, ③, ④, ⑤ and ⑥. In other words, the DNA sequence used for the synthesis of zeaxanthin is formed by adding the DNA sequence ⑥ to a DNA sequence used for the synthesis of β-carotene comprising the DNA sequences ①, ③, ④ and ⑤. The gene group includes the one in which the respective DNA sequences constructing the gene group are present on one DNA strand or on different DNA strands individually, or the one which is constructed by the combination of the aforementioned ones according to necessities.

In the case that a plurality of DNA sequences are present on one DNA strand, the arrangement order and direction of the aforementioned DNA sequences ①, ③, ④, ⑤ and ⑥ may be optional provided that the genetic information is capable of expression, that is to say respective genes in a host are in a state of being transcribed and translated appropriately.

The biosynthetic pathway of zeaxanthin in *E. coli* is explained as follows: geranylgeranyl pyrophosphate which is a substrate originally present in *E. coli* is converted into product phytoene by the enzyme encoded by the DNA sequence ⑤ and the product is converted into lycopene by the enzyme encoded by the DNA sequence ④, and the lycopene is further converted into β-carotene by the enzyme encoded by the DNA sequence ③, and finally the β-carotene is converted into zeaxanthin by the enzyme encoded by the DNA sequence ⑥. The enzyme encoded by the DNA sequence ① converts farnesyl pyrophosphate into geranylgeranyl pyrophosphate and thus is necessary to increase the production of zeaxanthin.

Zeaxanthin is a xanthophyll whose color is in the spectrum ranging from yellow to orange, and it is an yellow pigment which is present in the seed of maize and has high safety for food. Zeaxanthin is contained in feeds for hen or colored carp and is an important pigment source for coloring them. In this connection, the zeaxanthin which was synthesized by the DNA sequences according to the present invention in the experimental example described below had the same stereochemistry as zeaxanthin described above.

One of the typical existing forms of the gene group and the individual DNA sequences is the same as defined in (1).

(4) Gene group used for the synthesis of zeaxanthin-diglucoside

The gene group used for the synthesis of zeaxanthin-diglucoside which is one of yellow-orange carotenoids is a DNA sequence comprising the aforementioned DNA sequences ①–⑥. In other words, the gene group used for the synthesis of zeaxanthin-diglucoside is formed by adding the DNA sequence ② to a DNA sequence used for the synthesis of zeaxanthin comprising the DNA sequences ①, ③, ④, ⑤ and ⑥. The gene group includes the one in which the respective DNA sequences constructing the gene group are present on one DNA strand or on different DNA strands individually, or the one which is constructed by the combination of the aforementioned ones according to necessities.

In the case that a plurality of DNA sequences are present on one DNA strand, the arrangement order and direction of the aforementioned DNA sequences ①–⑥ may be optional provided that the genetic information is capable of expression, that is to say respective genes in a host are in a state of being transcribed and translated appropriately.

One of the typical existing forms of the gene group and the individual DNA sequences is the same as defined in (1).

The biosynthetic pathway of zeaxanthin-diglucoside in *E. coli* is explained as follows: geranylgeranyl pyrophosphate which is a substrate originally present in *E. coli* is converted into product and the product phytoene by the enzyme encoded by the DNA sequence 5 is then converted into lycopene by the enzyme encoded by the DNA sequence ④, and the lycopene is further converted into β-carotene by the enzyme encoded by the DNA sequence ③, the β-carotene is then converted into zeaxanthin by the enzyme encoded by the DNA sequence ⑥, and the zeaxanthin is finally converted into zeaxanthin-diglucoside by the enzyme encoded by the DNA sequence ②. The enzyme encoded by the DNA sequence ① converts farnesyl pyrophosphate into geranylgeranyl pyrophosphate and thus is necessary to increase the production of zeaxanthin-diglucoside.

Zeaxanthin-diglucoside is a carotenoid glycoside having a high water solubility and a pigment which is soluble sufficiently in water at room temperature and exhibits clear yellow. Carotenoid pigments are generally hydrophobic and thus limited on their use as natural coloring materials in foods or the like. Therefore, zeaxanthin-diglucoside settles this defect. Zeaxanthin-diglucoside is isolated from edible plant saffron, *Croccus sativus* (Pure & Appl. Chem., 47, 121–128 (1976)), so that it is thought that its safety for food has been confirmed. Therefore, zeaxanthin-diglucoside is desirable as a yellow natural coloring material of foods or the like. In this connection, there has been heretofore no reports with reference to the isolation of zeaxanthin-diglucoside from microorganisms.

If carotenoid pigments such as lycopene, β-carotene, zeaxanthin and zeaxanthin-diglucoside are intended to be produced, the aforementioned DNA sequences ①, ④ and ⑤, the DNA sequences ①, ③, ④ and ⑤, the DNA sequences ①, ③, ④, ⑤ and ⑥, and the DNA sequences 1+e,crc +ee –⑥ are required, respectively, on using *E. coli* as the host. However, when a host other than *E. coli*, particularly the one which is capable of producing carotenoids is used, it has a high possibility of containing also carotenoid precursors at further downstream in the biosynthesis, so that all of the aforementioned DNA sequences ①, ④ and ⑤ (for the production of lycopene), all of the DNA sequences ①, ③, ④ and ⑤ (for the production of β-carotene), all of the DNA sequences ①, ③, ④, ⑤ and ⑥ (for the production of zeaxanthin), or all of the DNA sequences ①–⑥ (for the production of zeaxanthin-diglucoside) are not always required.

That is to say, only the DNA sequence(s) participating in the formation of an aimed carotenoid pigment from a carotenoid precursor present at the furthest downstream in the host may also be used in this case. Thus, when lycopene is intended to be produced as an aimed carotenoid in a host in which phytoene is preliminarily present, it is also possible to use only the DNA sequence ④ among the DNA sequences ①, ④ and ⑤.

It is also possible to make a host to produce related carotenoid pigment compounds such as phytoene from geranylgeranyl pyrophosphate by using only the DNA sequence ⑤ or, preferably, the DNA sequences ① and ⑤ of the present invention.

Acquirement of DNA sequences

A method for acquiring the DNA sequences ①-⑥ which contain the nucleotide sequences coding for the amino acid sequences of the respective enzymes is the chemical synthesis of at least a part of their strand by the method of polynucleotide synthesis. However, if it is taken into consideration that a number of amino acids are bonded, it would be more preferable than the chemical synthesis to acquire the DNA sequences from the DNA library of *Erwinia uredovora* 20D3 ATTC 19321 according to a conventional method in the field of genetic engineering, for example, the hybridization method with a suitable probe.

The individual DNA sequences or the DNA sequence comprising all of these sequences are thus obtained.

Transformant

The aforementioned gene group comprising a plurality of the DNA sequences ①-⑥ can be constituted by using the DNA sequences obtained as described above. The DNA sequence thus obtained contains genetic informations for making an enzyme participating in the formation of carotenoids, so that it can be introduced into an appropriate host by the biotechnological method to form a transformant and to produce an enzyme and in its turn a carotenoid pigment or a carotenoid pigment relating compound.

(1) Host

Plants and a variety of microorganisms, as far as a suitable host-vector system is present, can be the target of transformation by a vector comprising the aforementioned DNA sequences. However, the host is required to contain geranylgeranyl pyrophosphate which is a substrate compound of an enzyme for starting the carotenoid synthesis with use of the DNA sequences of the present invention, or a compound further downstream from it.

It is known that farnesyl pyrophosphate is synthesized by dimethylallyltransferase which is a common enzyme at the initial stage of the biosynthesis of not only carotenoids but also sterols or terpenes [J. Biochem., 72, 1101–1108 (1972)]. Accordingly, if a cell which cannot synthesize carotenoids can synthesize sterols or terpenes, it probably contains farnesyl pyrophosphate. It is believed that a cell contains at least one of sterols or terpenes.

Therefore, it is believed theoretically that almost all hosts are capable of synthesizing carotenoids by using the DNA sequences of the present invention as far as a suitable host-vector system is present.

As the hosts in which the host-vector system is present, there are mentioned plants such as *Nicotiana tabacum, Petunia hybrida* and the like, microorganism such as bacteria, for example *Escherichia coli, Zymomonas mobilis* and the like, and yeasts, for example *Saccharomyces cerevisiae* and the like.

(2) Transformation

It is confirmed for the first time by the present invention that the genetic informations present on the DNA sequences of the present invention has been expressed in microorganisms. However, the procedures or the methods for making the transformants (and the production of enzymes or in its turn carotenoid pigments or carotenoid pigment relating compounds by the transformants) are per se conventional in the fields of molecular biology, cell biology or genetic manipulation, and thus the procedures other than described below may be performed in accordance with these conventional techniques.

In order to express the gene of the DNA sequences according to the present invention in a host, it is necessary to insert the gene into a vector for introducing it into the host. As the vector used in this stage, there is used all of various known vectors such as pBI121 or the like for plants (*Nicotiana tabacum, Petunia hybrida*); pUC19, pACYC184 or the like for *E. coli;* pZA22 or the like for *Zymomonas mobilis* (see Japanese Patent Laid-Open Publication No. 228278/87); and YEp13 or the like for yeast.

On the other hand, it is necessary to transcribe the DNA sequence of the present invention onto mRNA in order to express the gene of the DNA sequence in the host. For this purpose, a promoter as a signal for the transcription may be integrated into the 5'-upstream region from the DNA sequence of the present invention. A variety of promoters such as CaMV35S, NOS, TR1', TR2' (for plants); lac, $Tc^r$, CAT trp (for *E. coli*); $Tc^r$, CAT (for *Zymomonas mobilis*); ADH1, GAL7, PGK, TRP1 (for yeast) and the like are known as for the promoters, and either of these promoters can be used in the present invention.

In the case of procaryote, it is necessary to place ribosome-binding site (SD sequence in *E. coli*) several base-upstream from the initiation codon (ATG).

In this connection, while the aforementioned manipulation is necessary for producing the enzyme protein, one or more of amino acids may be inserted into or added to the polypeptide which is illustrated in the specific ranges of FIGS. 1–6 (e.g. the polypeptide A–B illustrated in FIG. 1), one or more of amino acids may be deleted, or replaced, as described above.

The transformation of the host with the plasmid thus obtained can be conducted optionally by an appropriate method which is conventionally used in the fields of genetic manipulation or cell biology. As for the general matters, there can be referred to appropriate publications or reviews; for example as for the transformation of microorganisms, T. Maniatis, E. F. Fritsch and J. Sambrook: "Molecular Cloning A Laboratory Manual", Cold Spring Harbor Laboratory (1982).

The transformant is the same as the host used, in its genotype, phenotype or bacteriological properties but for the new trait derived from the genetic information introduced by the DNA sequence of the present invention (that is, the production of an enzyme participating in the carotenoid formation and the synthesis of carotenoids or the like by the enzyme), the trait derived from the vector used and the deletion of the trait corresponding to the deletion of a part of the genetic information of the vector which might be caused on the recombination of genes. *Escherichia coli* JM109 (pCAR1) which is an example of the transformant according to the present invention is deposited as FERM BP-2377.

Expression of genetic information/production of carotenoids

The clone of the transformant obtained as described above produces mainly in the transformant an enzyme participating in the carotenoid formation, and a variety of carotenoids or carotenoid pigment relating compounds are synthesized by the enzyme.

Culture or the culturing condition of the transformant is essentially the same as those for the host used.

Carotenoids can be recovered by the methods, for example, illustrated in Experimental Examples 3 and 4 below.

Furthermore, each enzyme protein coded by each DNA sequence of the present invention is produced mainly in the cell in the case of the transformation of *E. coli*, and it can be recovered by an appropriate method.

BRIEF DESCRIPTION OF THE DRAWINGS

FIGS. 1–6 illustrate the nucleotide sequences in the DNA sequences ①–⑥ in coding regions, and the amino acid sequences of proteins to be encoded, respectively, FIG. 7 illustrates the KpnI-HindIII fragment which was acquired from *Erwinia uredovora* 20D3 ATCC 19321 and relates to the biosynthesis of carotenoids, that is the complete nucleotide sequence of the 6918 bp DNA sequence containing the DNA sequences in FIGS. 1–6, and FIG. 8 illustrates the function of the polypeptides encoded by the aforementioned DNA sequences ①–⑥. +de

EXPERIMENTS

All of strains used in the following experiments are deposited in ATCC or other deposition organizations and are freely available.

Experimental Example 1: Cloning of a gene cluster participating in the biosynthesis of a yellow pigment (referred to hereinafter as yellow pigment-synthesizing gene cluster)

(1) Preparation of total DNA

Total DNA was prepared from the cells of *Erwinia uredovora* 20D3 ATCC 19321 which had been proliferated until the early-stationary phase in 100 ml of LB medium (1% tryptone, 0.5% yeast extract, 1% NaCl). Penicillin G (manufactured by Meiji Seika) was added to the culture medium so that it has a concentration of 50 units/ml in the medium before 1 hour of the harvest of the cells. After harvesting the cells by centrifugation, this was washed with the TES buffer (20 mM tris, 10 mM EDTA, 0.1M NaCl, pH 8), heat treated at 68° C. for 15 minutes and suspended in Solution I (50 mM glucose, 25 mM Tris, 10 mM EDTA, pH 8) containing 5 mg/ml of lysozyme (manufactured by Seikagaku Kogyo) and 100 µg/ml of RNase A (manufactured by Sigma). The suspension was incubated at 37° C. for a period of 30 minutes—1 hour, and pronase E (manufactured by Kaken Seiyaku) was added so that it had a concentration of 250 µg/ml before incubation at 37° C. for 10 minutes. Sodium N-lauroylsarcosine (manufactured by Nacalai tesque) was added so as it had the final concentration of 1%, and the mixture was agitated before incubation at 37° C. for several hours. Extraction was conducted several times with phenol/chloroform. While ethanol in volume of 2 equivalents was slowly added, the resulting total DNA was wound around a glass stick, rinsed with 70% ethanol and dissolved in 2 ml of TE buffer (10 mM Tris, 1 mM EDTA, pH 8) to give the total DNA preparation.

(2) Construction of an *Escherichia coli* cosmid library and acquirement of *E. coli* transformants producing yellow pigments Incubation was conducted with 1 unit of restriction enzyme Sau3AI per 26 µm of the total DNA preparation at 37° C. for 30 minutes before the inactivation treatment of the restriction enzyme at 68° C. for 10 minutes. Many fragments partially digested with Sau3AI were obtained in the neighbourhood of 40 kb under this condition. After the ethanol precipitation of this reaction solution, this half portion was mixed with 2.5 µg of cosmid pJB8 which had been digested with BamHI and treated with alkaline phosphatase and 0.2 µg of a pJB8 SalI-BamHI right arm fragment (smaller fragment) which had been recovered from a gel, and 40 µl of the total amount was subjected to ligation reaction with T4 DNA ligase at 12° C. for 2 days. In this connection, the cosmid pJB8 had been previously purchased from Amersham. Restriction enzymes and enzymes used for genetic manipulation were purchased from Boehringer-Mannheim, Takara Shuzo or Wako Pure Chemical Industries. This DNA in which the ligation reaction had been thus performed was used for in vitro packaging with a Gigapack Gold (manufactured by Stratagene, marketed from Funakoshi) to give a large amount of phage particles sufficient for construction of a cosmid library. The phage particles were infected to *Escherichia coli* DH1 (ATCC 33849). After the cells of *E. coli* DH1 infected were diluted so as to be several hundred colonies per plate, they were plated on a LB plate, cultured at 37° C. overnight and further at 30° C. for 6 hours or more. As a result, *E. coli* transformants producing yellow pigments appeared in a proportion of one colony per about 1,100 colonies. These *E. coli* transformants producing yellow pigments contained plasmids in which 33–47 kb Sau3AI partial digestion fragments were inserted into the pJB8.

(3) Location of a yellow pigment-synthesizing gene cluster

A yellow pigment-synthesizing gene cluster was inserted into the pJB8 as the 33–47 kb SaU3AI partial digestion fragments. One of these fragments was further subjected to partial digestion with Sau3AI, ligated to the BamHI site of the *E. coli* vector pUC19 (purchased from Takara Shuzo), and used to transform *Escherichia coli* JM109 (manufactured by Takara Shuzo). To locate the yellow pigment-synthesizing gene cluster, plasmid DNA's were prepared from 50 *E. coli* transformants producing yellow pigments which appeared in the LB plate containing ampicillin, and analyzed by agarose gel electrophoresis. As a result, it was found that the smallest inserted fragment was of 8.2 kb. The plasmid containing this 8.2 kb fragment was named as pCAR1 and *E. coli* JM109 harboring this plasmid was named as *Escherichia coli* JM109 (pCAR1). This strain produced the same yellow pigments as those of *E. uredovora*. The 8.2 kb fragment contained a KpnI site in the neighbourhood of the terminal at the lac promoter side and a HindIII site in the neighbourhood at the opposite side. After the 8.2 kb fragment was subjected to double digestion with KpnI/HindIII (HindIII was partially digested; the 8.2 kb fragment had two HindIII sites), the KpnI-HindIII fragment (6.9 kb) was recovered from a gel and ligated to the KpnI-HindIII site of pUC18 (this hybrid plasmid was named as pCAR15). Upon the transformation of *E. coli* JM109, the *E. coli* transformant exhibited yellow and produced the same yellow pigments as those of *E. uredovora*. Accordingly, it was found out that the genes required for the yellow pigment production was located on the KpnI-HindIII fragment (6.9 kb). That is to say, the fragment carrying the yellow pigment-synthesizing genes was capable of being reduced to a 6.9 kb in size.

Experimental Example 2: Analysis of the yellow pigment-synthesizing gene cluster (1) Determination of the nucleotide sequence of the yellow pigment-synthesizing gene cluster The complete nucleotide sequence of the 6.9 kb KpnI-HindIII fragment was determined by the kilo-sequence method using Deletion kit for kilo-sequence (manufactured by Takara Shuzo) and the dideoxy method according to Proc. Natl. Acad. Sci. USA, 74 5463–5467 (1977). As a result, it was found that the KpnI-HindIII fragment containing the yellow pigment-synthesizing genes (DNA strand) was 6918 base pairs (bp) in length and its GC content was 54%. The complete nucleotide sequence was shown in FIG. 7(a)–(g). The KpnI site is represented by the base number 1.

(2) Elucidation of yellow pigment-synthesizing gene cluster

The HindIII side of the 6918 bp fragment (DNA strand) containing the yellow pigment-synthesizing genes (right terminal side in FIG. 7) was deleted with Deletion kit for kilo-sequence. A hybrid plasmid (designated pCAR25) was constructed by inserting a 1–6503 fragment, which was obtained by deletion from the HindIII site to nucleotide position 6504, into pUC19. *E. coli* JM109 harboring pCAR25 [referred to hereinafter as *E. coli* (pCAR25)] exhibited yellow and produced the same yellow pigments as those of *E. uredovora*. Therefore, it was thought that the region from the base number 6504 to 6918 in FIG. 7 was not required for yellow pigment production. The nucleotide sequence in the region from the base number 1 to 6503 in the 6918 bp DNA sequence containing the yellow pigment-synthesizing genes was analyzed. As a result, it was found that there were six open reading frames (ORFs). That is to say, there were an ORF coding for a polypeptide with a molecular weight of 32,583 from the base number 225 to 1130 (referred to as ORF1, which corresponds to A–B in FIGS. 1 and 7), an ORF coding for a polypeptide with a molecular weight of 47,241 from the base number 1143–2435 (referred to as ORF2, which corresponds to C–D in FIGS. 2 and 7), an ORF coding for a polypeptide with a molecular weight of 43,047 from the base number 2422 to 3567 (referred to as ORF3, which corresponds to E–F in FIGS. 3 and 7), an ORF coding for a polypeptide with a molecular weight of 55,007 from the base number 3582 to 5057 (referred to as ORF4, which corresponds to G–H in FIGS. 4 and 7), an ORF coding for a polypeptide with a molecular weight of 33,050 from the base number 5096 to 5983 (referred to as ORF5, which corresponds to I–J in FIGS. 5 and 7), and an ORF coding for a polypeptide with a molecular weight of 19,816 from the base number 6452 to 5928 (referred to as ORF6, which corresponds to K–L in FIGS. 6 and 7. Only this ORF6 has the opposite orientation with the others). In this connection, each ORF contained at positions several base-upstream from its initiation codon the SD (Shine-Dalgarno) sequence which is homologous with the 3'-region of 16S ribosomal RNA of *E. coli*. Thus, it was thought that polypeptides were in fact synthesized in *E. coli* by these six ORFs. This was confirmed by the following in vitro transcription-translation experiment.

That is to say, the in vitro transcription-translation analysis was carried out with DNA in which the plasmid pCAR25 containing ORF1–ORF6 had been digested with ScaI and with DNAs in which respective fragments containing respective ORFs (containing the SD sequence) of ORF1–ORF6 had been digested with appropriate restriction enzymes, isolated, inserted into pUC19 or pUC18 so that it was subjected to transcriptional read-through from a lac promoter, and then digested with ScaI. In this experiment, a Prokaryotic DNA-directed translation kit manufactured by Amersham was used. As a result, it was confirmed that the bands of polypeptides corresponding to the aforementioned respective ORFs were detected as the transcription-translation products.

Moreover, all of six ORFs were necessary for production of the same yellow pigments as those of *E. uredovora* as described below (Experimental Examples 3, 4 and 5). From these results, ORF1, ORF2, ORF3, ORF4, ORF5 and ORF6 were designated as zexA, zexB, zexC, zexD, zexE and zexF genes, respectively.

The base numbers in FIGS. 1–6 were represented on the basis of the KpnI site in FIG. 7 as the base number 1 and correspond to each other. The marks A-L in FIGS. 1 –6 correspond to the marks A-L in FIG. 7. The DNA sequence from K to L in FIG. 6 was that of the complementary strand of the DNA sequence from K to L in FIG. 7. That is to say, the DNA sequence illustrated in FIG. 6 has the opposite orientation in transcription with the DNA sequences in FIGS. 1–5 in the original DNA sequence (FIG. 7).

(3) Analysis of homology by the DNA-DNA hybridization method

Total DNA of *Erwinia herbicola* Eho 10 ATCC 39368 was prepared in the same manner as in Experimental Example 1 (1). A 7.6 kb fragment containing the DNA sequence in FIG. 7 was cut out from the hybrid plasmid pCAR1 by KpnI digestion and labeled with DNA labeling & detection kit nonradioactive (manufactured by Boehringer-Mannheim) according to the DIG-ELISA method to give probe DNA. The homology of total DNAs (intact or KpnI digested) of *E. herbicola* Eho 10 ATCC 39368 and *E. uredovora* 20D3 ATCC 19321 with this probe DNA was analyzed by the DNA-DNA hybridization method with the aforementioned DNA labeling & detection kit nonradioactive. As a result, the probe DNA was hybridized strongly with total DNA of the latter *E. uredovora* 20D3 ATCC 19321, but not at all with total DNA of the former *E. herbicola* Eho 10 ATCC 39368. Also, the restriction map deduced from the DNA sequence in FIG. 7 was quite different from that reported in J. Bacteriol., 168, 607–612 (1986). It was concluded from the above described results that the DNA sequence in FIG. 7, that is, the DNA .sequences useful for the synthesis of carotenoids according to the present invention exhibits no homology with the DNA sequence containing the yellow pigment-synthesizing genes of *E. herbicola* Eho 10 ATCC 39368.

Experimental Example 3: Analysis of yellow pigments

*E. coli* (pCAR25) produced the same yellow pigments as those of *E. uredovora* 20D3 ATCC 19321 and *E. herbicola* Eho 10 ATCC 39368, and its yield was 5 times higher than those of the former and 6 times higher than those of the latter (per dry weight). The cells harvested from 8 liters of 2×YT medium (1.6% tryptone, 1% yeast extract, 0.5% NaCl) were extracted once with 1.2 liter of methanol. The methanol extract was evaporated to dryness, dissolved in methanol, and subjected to thin layer chromatography (TLC) with silica gel 60 (Merck) (developed with chloroform : methanol=4:1). The yellow pigments were separated into 3 spots having Rf values of 0.93, 0.62 and 0.30 by TLC. The yellow (to orange) pigment at the Rf value of 0.30 which was the strongest spot was scraped up from the TLC plate, extracted with a small amount of methanol, loaded on a Sephadex LH-20 column for chromatography [30 cm×3.0 cm (Ø)] and developed and eluted with methanol to give 4 mg of a pure product. The yellow (to orange) pigment obtained was sparingly soluble in organic solvents other than methanol and easily soluble in water, so that it was suggested that it might be a carotenoid glycoside. Such suggestion was also supported from a molecular weight of 892 by FD-MS spectrum (the mass of this pigment was larger than that of zeaxanthin (described hereinafter) by the mass of two glucose). When this substance was hydrolyzed with 1N HCl at 100° C. for 10 minutes, zeaxanthin was obtained. Then, acetylation was conducted according to the usual method. That is, the substance was dissolved in 10 ml of pyridine, large excess of acetic anhydride was added, and the mixture was stirred at room temperature and left standing overnight. After the completion of reaction, water was added to the mixture and chloroform extraction was carried out. The chloroform extract was concentrated and loaded on a silica gel column [30 cm×3.0 cm (Ø)] for chromatography to develop and elute with chloroform. Measurement of $^1$H-NMR gave the spectrum identical with the tetraacetyl derivative of zeaxanthin-β-diglucoside [Helvetica Chimica Acta, 57, 1641–1651 (1974)], so that the substance was identified as zeaxanthin-β-diglucoside (its structure being illustrated below).

The yield was 1.1 mg/g dry weight. The substance had a solubility of at least 2 mg in 100 ml of water and methanol, and water was superior to methanol in solubility of the substance. The substance had low solubilities in chloroform and acetone, and its solubilities were 0.5 mg in 100 ml of these solvents.

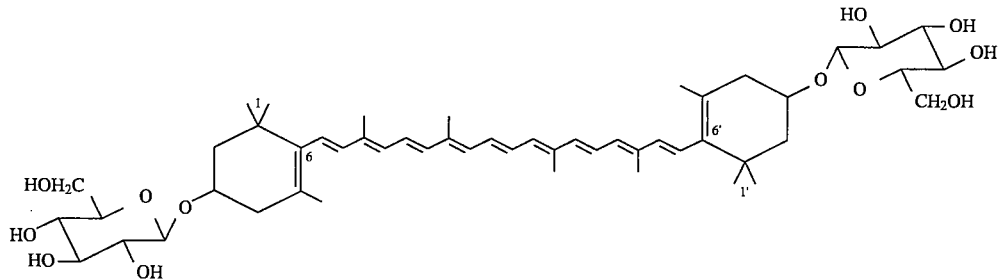

Experimental Example 4: Analysis of the metabolic intermediates of carotenoids (1) Construction of various deletion plasmids A hybrid plasmid (designated as pCAR16) was constructed by inserting a 1-6009 fragment, which was obtained by deletion to nucleotide position 6010 from the HindIII site (right terminal in FIG. 7) of the 6918 bp fragment containing the yellow pigments-synthesizing genes (DNA strand) (FIG. 7) using Deletion kit for kilo-sequence. pCAR16 contains the genes from zexA to zexE. Various deletion plasmids were constructed, as shown in Table 1, on the basis of the pCAR16 and the aforementioned hybrid plasmid pCAR25 (containing genes from zexA to zexF.

Table 1: Construction of various deletion plasmids

The number within parentheses behind the name of respective restriction enzymes represents the number of base at the initial recognition site of the restriction enzyme. The base numbers correspond to those in FIGS. 1–6 and FIG. 7. Analysis of the metabolic intermediates of carotenoids was performed using the transformants of *E. coli* JM109 by various deletion plasmids [referred to hereinafter as *E. coli* (name of plasmid)].

TABLE 1

| Plasmid | Construction method | Genes functioning |
|---|---|---|
| pCAR25 | See text | zexA zexB zexC zexD zexE zexF |
| pCAR25delB | Frame shift in BstEII (1235) of pCAR25 | zexA zexC zexD zexE zexF |
| pCAR16 | See text | zexA zexB zexC zexD zexE |
| pCAR16delB | Frame shift in BstEII (1235) of pCAR16 | zexA zexC zexD zexE |
| pCAR16delC | Frame shift in SnaBI (3497) of pCAR16 | zexA zexB zexD zexE |
| pCAR-ADE | Deletion of the BstEII (1235) - SnaBI (3497) fragment from pCAR16 | zexA zexD zexE |
| pCAR-ADEF | Deletion of the BstEII (1235) - SnaBI (3497) fragment from pCAR25 | zexA zexD zexE zexF |
| pCAR25delD | Frame shift in BamHI (3652) of pCAR25 | zexA zexB zexC zexE zexF |
| pCAR-AE | Deletion of the BstEII (1235) - BamHI (3652) fragment from pCAR16 | zexA zexE |
| pCAR-A | Insertion of the KpnI (1) - BstEII (1235) fragment in pUC19 | zexA |

TABLE 1-continued

| Plasmid | Construction method | Genes functioning |
|---|---|---|
| pCAR-E | Insertion of the Eco52I (4926) - 6009 fragment in pUC19 | zexE |
| pCAR25delE | Frame shift in MluI (5379) of pCAR25 | zexA zexB zexC zexD zexF |
| pCAR25delA | Frame shift in AvaI (995) of pCAR25 | zexB zexC zexD zexE zexF |
| pCAR-CDE | Insertion of the SalI (2295) - 6009 fragment in pUC19 | zexC zexD zexE |

(2) Identification of zeaxanthin

The cells harvested from 3 liters of 2×YT medium of *E. coli* (pCAR25delB) (exhibiting orange) were extracted twice with 400 ml portions of acetone at low temperature, concentrated, then extracted with chloroform:methanol (9:1) and evaporated to dryness. This was subjected to silica gel column chromatography [30 cm×3.0 cm (Ø)]. After the column was washed with chloroform, an orange and was eluted with chloroform:methanol (100:1). This pigment was dissolved in ethanol, recrystallized at low temperature to give 8 mg of a pure product. The analysis by its UV-visible absorption, $^1$H-NMR, $^{13}$C-NMR and FD-MS (m/e 568) spectra revealed that this substance had the same structure except for stereochemistry as zeaxanthin (β, β-carotene-3, 3'-diol). It was then dissolved in diethyl ether : isopentane : ethanol (5:5:2), and the CD spectrum was measured. As a result, it was found that this substance had a 3R,3'R-stereochemistry [Phytochemistry, 27, 3605–3609 (1988)]. Therefore, it was identified as zeaxanthin (β, β-carotene-3R,3'R-diol), of which the structure is illustrated below. The yield was 2.2 mg/g dry weight. This substance corresponded to the yellow pigment having an Rf value of 0.93 in Experimental Example (1).

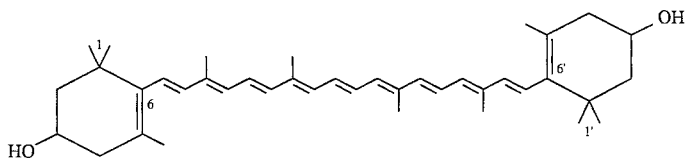

(3) Identification of β-carotene

The cells harvested from 3 liters of LB medium of *E. coli* (pCAR16) (exhibiting orange) were extracted 3 times with 500 ml portions of cold methanol at low temperature and the methanol extract was further extracted with 1.5 liter of hexane. The hexane layer was concentrated and subjected to silica gel column chromatography [30 cm×3.0 cm (∅)]. Development and elution were conducted with hexane:ethyl acetate (50:1) to collect an orange band. The orange fraction was concentrated and recrystallized from ethanol to give 8 mg (reduced weight without moisture). This substance was presumed to belong to β-carotene from its UV-visible absorption spectrum, and a molecular weight of 536 by FD-MS spectrum also supported this presumption. Upon comparing this substance with the authentic sample (Sigma) of β-carotene by $^{13}$C-NMR spectrum, all of chemical shifts of carbons were identical with each other. Thus, this substance was identified as β-carotene (all-trans-β, β-carotene, of which the structure was illustrated below). It was also confirmed by the similar method that *E. coli* (pCAR16delB) accumulated the same β-carotene as described above. Its yield was 2.0 mg/g dry weight, which corresponded to 2–8 times (per dry weight) of the total carotenoid yield in carrot (Kintokininjin) culture cells described in Soshikibaiyou (The Tissue Culture), 13, 379–382 (1987).

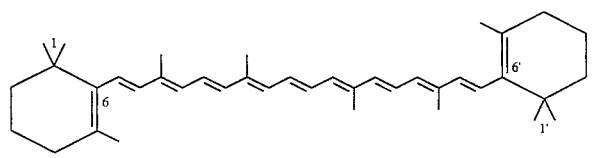

(4) Identification of lycopene

The cells harvested from 3 liters of LB medium of *E. coli* (pCAR16delC) (exhibiting red) were extracted once with 500 ml of cold methanol at low temperature, and the precipitate by centrifugation was extracted again with 1.5 liter of chloroform. The chloroform layer was concentrated and subjected to silica gel chromatography [30 cm×3.0 cm (∅)]. Development and elution were conducted with hexane:chloroform (1:1) to collect a red band. This fraction was concentrated. This substance was presumed to belong to lycopene from its UV-visible absorption spectrum, and a molecular weight of 536 by FD-MS spectrum also supported this presumption. Upon comparing this substance with the authentic sample (Sigma) of lycopene by $^1$H-NMR spectrum, all of chemical shifts of hydrogens were identical with each other. When, this substance and the authentic sample were subjected to TLC with silica gel 60 (Merck) [developed with hexane:chloroform (50:1)] and with RP-18 [developed with methanol: chloroform (4:1)], the displacement distances of these samples were completely equal to each other. Thus this substance was identified as lycopene (all-trans-ψ, ψ-carotene, of which the structure was illustrated below). It was also confirmed by the similar method that *E. coli* (pCAR-ADE) and *E. coli* (pCAR-ADEF) accumulated the same lycopene as described above. The yield of the former was 2.0 mg/g dry weight, which corresponded to 2 times (per dry weight) of the total carotenoid yield in a hyperproduction derivative of carrot (Kintokininjin) culture cells described in Soshikibaiyou (The Tissue Culture), 13, 379–382 (1987).

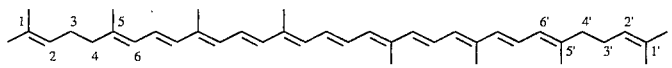

(5) Identification of phytoene

The cells harvested from 1.5 liter of 2×YT medium of *E. coli* (pCAR-AE) were extracted twice with 200 ml portions of acetone and twice with 100 ml portions of hexane, and evaporated to dryness. This was subjected to silica gel chromatography [30 cm×3.0 cm (∅)]. Development and elution were conducted with hexane: chloroform (1:1) to collect a band which had a strong UV absorption, and it was confirmed to be phytoene by its UV absorption spectrum. It was further subjected to LH-20 column chromatography [30 cm×3.0 cm (∅)]. Development and elution were conducted with chloroform:methanol (1:1) to give 4 mg of a pure product. The comparison of the $^1$H-NMR spectrum of this substance with the $^1$H-NMR spectra of trans- and cis-phytoen (J. Magnetic Resonance, 10, 43–50 (1973)) showed this substance to be a mixture of the trans- and cis-isomers. Isomerization from trans-isomer to cis-isomer hardly occurs, and thus it was judged that such a mixture was produced as a result of cis-trans isomerization in the course of the purification. Therefore, it was concluded that the original phytoene was the cis-type phytoene 15, 15' cisphytoene, whose structure is shown below. It was also confirmed by the similar method that *E. coli* (pCAR25delD) accumulated the same phytoene as described above.

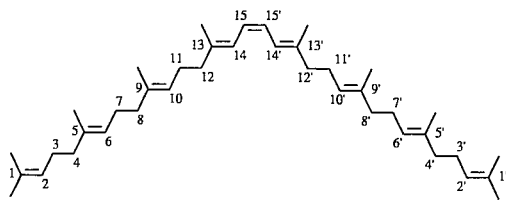

Experimental Example 5: Identification of carotenoid biosynthesis genes

From the facts that E. coli (pCAR25) produced zeaxanthin-diglucoside and that E. coli (pCAR25delB) harboring a plasmid, in which zexB had been removed from pCAR25, accumulated zeaxanthin, it was found that the zexB gene encoded the glycosylation enzyme which was capable of converting zeaxanthin into zeaxanthin-diglucoside. Similarly, from the fact that E. coli (pCAR16delB) harboring a plasmid, in which zexF had been removed from pCAR25delB, accumulated β-carotene, it was found that the zexF gene encoded the hydroxylation enzyme which was capable of converting β-carotene into zeaxanthin. Similarly, from the fact that the E. coli (pCAR-ADE) harboring a plasmid, in which zexC had been removed from pCAR16delB, accumulated lycopene, it was found that the zexC gene encoded the cyclization enzyme which was capable of converting lycopene into β-carotene. Also, E. coli (pCAR-ADEF) carrying both of the zexA, zexD and zexE genes required for producing lycopene and the zexF gene encoding the hydroxylation enzyme was able to synthesize only lycopene. This demonstrates directly that the hydroxylation reaction in carotenoid biosynthesis occurs after the cyclization reaction. Further, from the facts that E. coli (pCAR-ADE) accumulated lycopene and that E. coli (pCAR-AE) harboring a plasmid, in which the zexD gene had been removed from pCAR-ADE, accumulated phytoene, it was found that the zexD gene encoded the desaturation enzyme which was capable of converting phytoene into lycopene. E. coli (pCAR-A) and E. coli (pCAR-E) were not able to produce phytoene. It was thought from this result that both of the zexA and zexE genes were required for producing phytoene in E. coli. zexE and zexA were identified, by comparing their putative amino acid sequence with those of crtB and crtE gene products in a photo synthetic bacterium Rhodobacter capsuratus [Mol. Gen. Genet., 216, 254–268 (1988)]. From these analyses described above, all of the six genes have been identified and the biosynthetic pathway of carotenoids have also been clear.

E. coli (pCAR25delE) accumulated no detectable carotenoid intermediate, while E. coli (pCAR25delA) and E. coli (pCAR-CDE) were able to produce a small amount of carotenoids. That is to say, E. coli (pCAR25delA) and E. coli (pCAR-CDE) produced 4% of zeaxanthin-diglucoside and 2% of β-carotene as compared with the E. coli (pCAR25) and the E. coli (pCAR16delB), respectively. It is not clear at this moment, however, why phytoene was not detected in E. coli (pCAR-E) carrying the crtB gene.

As described above, the detailed biosynthetic pathway of carotenoids including general and famous carotenoids such as lycopene, β-carotene and zeaxanthin and water soluble carotenoid such as zeaxanthin-diglucoside were for the first time elucidated, and the gene cluster useful for these biosynthesis was capable of being acquired for the first time. In this connection, lycopene, β-carotene and zeaxanthin which were produced by the genes in the aforementioned Experimental Examples were stereochemically identical with those derived from higher plants [T. W. Goodwin: "Plant Pigments", Academic Press (1988)].

As for zeaxanthin-diglucoside, the isolation from a plant was only reported [Pure & Appl. Chem., 47, 121–128 (1976)], but its isolation from microorganisms has not been reported.

Experimental Example 6: Synthesis of carotenoids in Zymomonas

ZYMOMONAS

Zymomonas mobilis is a facultative anaerobic ethanol-producing bacterium. It has a higher ethanol producing rate than that of yeast (Saccharomyces cerevisiae), so that it is preferable as a fuel alcohol-producing bacterium in future. Also, Zymomonas has a special metabolic pathway, Entner-Doudoroff but not glycolytic pathway and cannot produce carotenoids. In order to add further values to this bacterium, the carotenoid biosynthesis genes were introduced into Zymomonas.

The 7.6 kb fragment containing the DNA sequence shown in FIG. 7 was cut out from the hybrid plasmid pCAR1 by KpnI digestion and treated with DNA polymerase I (Klenow enzyme). The fragment thus treated was ligated to the EcQRV site of the cloning vector pZA22 for Zymomonas [see Agric. Biol. Chem., 50, 3201–3203 (1986) and Japanese Patent Laid-Open Publication No. 228278/87]to construct a hybrid plasmid pZACAR1. Also, the 1–6009 fragment in the DNA sequence in FIG. 7 was cut out from pCAR16 by KpnI/EcRI digestion and treated with DNA polymerase I (Klenow enzyme). The fragment thus treated was ligated to the EcoRV site of pZA22 to construct a hybrid plasmid pZACAR16. The orientation of the inserted fragments in these plasmids were opposite with the orientation of the Tc$^r$ gene on taking the orientation in FIG. 7 as the normal one. These plasmids were introduced into Z. mobilis NRRL B-14023 by conjugal transfer with the helper plasmid pRK2013 (ATCC 37159) and stably maintained in this strain. Z. mobilis NRRL B-14023 in which pZACAR1 and pZACAR16 had been introduced exhibited yellow, and produced zeaxanthin-diglucoside in an amount of 0.28 mg/g dry weight and β-carotene in an amount of 0.14 mg/g dry weight, respectively. Therefore, carotenoids were successfully produced in Zymomonas by the carotenoid biosynthesis genes according to the present invention.

DEPOSITION OF MICROORGANISM

Microorganism relating to the present invention is deposited at Fermentation Research Institute, Japan as follows:
Microorganism Accession number Date of deposit Escherichia coli FERM BP 2377 Apr. 11, 1989 JM109 (pCAR1)

What is claimed is:

1. An isolated and purified DNA encoding a polypeptide which has an enzymatic activity involved in carotenoid biosynthesis and whose amino acid sequence is from A to B of the amino acid sequence shown in FIGS. 1(a) and (b).

2. An isolated and purified DNA encoding a polypeptide which has an enzymatic activity for converting zeaxanthin into zeaxanthin-diglucoside and whose amino acid sequence is from C to D of the amino acid sequence shown in FIGS. 2(a) and (b).

3. An isolated and purified DNA encoding a polypeptide which has an enzymatic activity for converting lycopene into β-carotene and whose amino acid sequence is from E to F of the amino acid sequence shown in FIGS. 3(a) and (b).

4. An isolated and purified DNA encoding a polypeptide which has an enzymatic activity for converting phytoene into lycopene and whose amino acid sequence is from G to H of the amino acid sequence shown in FIGS. 4(*a*), (*b*) and (*c*).

5. An isolated and purified DNA encoding a polypeptide which has an enzymatic activity for utilizing geranylgeranyl pyrophosphate as a substrate in a carotenoid biosynthesis and whose amino acid sequence is from I to J of the amino acid sequence shown in FIGS. 5(*a*) and (*b*).

6. An isolated and purified DNA encoding a polypeptide which has an enzymatic activity for converting β-carotene into zeaxanthin and whose amino acid sequence is from K to L of the amino acid sequence shown in FIG. 6.

* * * * *